United States Patent
Soegaard et al.

(10) Patent No.: US 6,962,694 B1
(45) Date of Patent: Nov. 8, 2005

(54) CYTOLYSIS OF TARGET CELLS BY SUPERANTIGEN CONJUGATES INDUCING T-CELL ACTIVATION

(75) Inventors: Morten Soegaard, Kopenhamn (DK); Lars Abrahmsen, Bromma (SE); Peter Lando, Malmo (SE); Goran Forsberg, Eslov (SE); Terje Kalland, Loddekopinge (SE); Mikael Dohlsten, Lund (SE)

(73) Assignee: Active Biotech AG, Lund (SE)

( * ) Notice: Subject to any disclaimer, the term of this patent is extended or adjusted under 35 U.S.C. 154(b) by 0 days.

(21) Appl. No.: 09/463,470

(22) PCT Filed: Jul. 21, 1998

(86) PCT No.: PCT/EP98/04219

§ 371 (c)(1),
(2), (4) Date: Jan. 21, 2000

(87) PCT Pub. No.: WO99/04820

PCT Pub. Date: Feb. 4, 1999

Related U.S. Application Data
(60) Provisional application No. 60/053,211, filed on Jul. 11, 1997.

(30) Foreign Application Priority Data
Nov. 14, 1997 (SE) .............................. 9704170

(51) Int. Cl.[7] ..................... A61K 39/00; A61K 39/395; A61K 45/00
(52) U.S. Cl. ................ 424/85.2; 424/178.1; 424/182.1; 424/183.1; 424/195.11; 424/197.11; 530/391.7
(58) Field of Search ............................ 424/85.2, 178.1, 424/182.1, 183.1, 197.11, 195.11; 530/391.7

(56) References Cited

U.S. PATENT DOCUMENTS 5,705,151 A * 1/1998 Dow et al.

6,514,498 B1 * 2/2003 Antonsson et al. ...... 424/178.1

FOREIGN PATENT DOCUMENTS

| WO | 9601650 | * 1/1996 |
| WO | 9736932 | * 10/1997 |

OTHER PUBLICATIONS

Belfrage et al, Immunology, 90, 183–188, 1997.*
Lando et al, Journal of Immunology, 157, 2857–2863, 1996.*

* cited by examiner

Primary Examiner—David Saunders
(74) Attorney, Agent, or Firm—Fulbright & Jaworski LLP; David L. Fox

(57) ABSTRACT

A method for inactivating target cells in the presence of T cells by bringing the two types of cells in contact with a superantigen (SAG) in the presence of an immune modulator, characterized in that at least one of the superantigen and the immune modulator is in the form of a conjugate between a "free" superantigen (Sag) and a moiety targeting the conjugate to the target cells. A superantigen conjugate complying with the formula (1) $(T)_x(Sag)_y(IM)_z$; a) T is a targeting moiety, Sag corresponds to a free superantigen, IM is an immune modulator that is not a superantigen and T, Sag and IM are linked together via organic linkers B; b) x, y and z are integers that typically are selected among 0–10 and represent the number of moieties T, Sag and IM, respectively, in a given conjugate molecule, with the provision that y>0 and also one or both of x and z>0. The superantigen conjugate is preferably a triple fusion protein. A targeted immune modulator, characterized in that it is a conjugate between a targeting moiety (T''') and a modified immune modulator (IM'''). The conjugate complies with a formula analogous to formula (1) except for the imperative presence of the modified immune modulator. A superantigen moiety may be present. A DNA molecule encoding a superantigen and an immune modulator.

12 Claims, 15 Drawing Sheets

CYTOLYSIS OF TARGET CELLS BY SUPERANTIGEN CONJUGATES INDUCING T-CELL ACTIVATION

Figure 1:
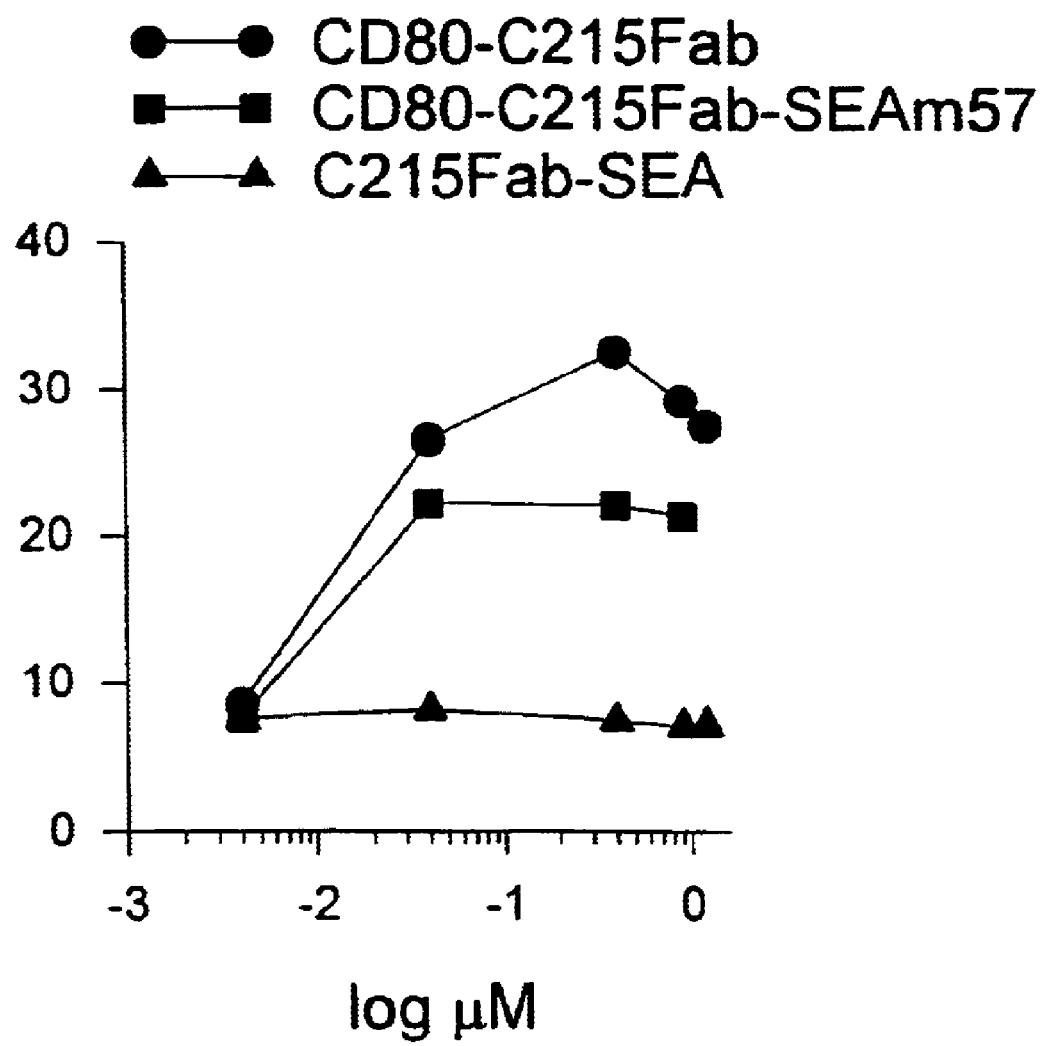

This application is the National Stage Application of International Application No. PCT/EP98/04219 filed on Jul. 2, 1998 which claims priority to Swedish Application No. SE-97041710-1 filed on Nov. 14, 1997 and U.S. Provisional Application No. 60/053,211 filed on Jul. 11, 1997.

FIELD OF THE INVENTION

The present invention relates to inactivation/cytolysis of target cells caused by T cells activated by functional superantigens. Cytolysis can be applied to therapy and to in vitro assays.

DEFINITIONS

Superantigens. According to the very first definition (around 1988–1993), superantigens are bacterial or viral proteins capable of binding to MHC class II antigens without prior intracellular processing and activate T cells by binding to the Vβ-chain variable region (Vβ) of the T cell receptor (TCR). The binding leads to a Vβ family restricted activation of a relatively large proportion/subset of T cells and lysis of MHC Class II expressing cells (superantigen dependent cell-mediated cytolysis=SDCC). Normally the superantigen activated subset of T cells constitutes about 1–30% of the total amount of T cells of an individual.

Well known wild-type superantigens according to the definition above are the staphylococcal enterotoxins (SEA, SEB, SEC1, SEC2, SED, SEE and SEH). Further examples are Toxic Shock Syndrome Toxin 1 (TSST-1, also of staphylococcal origin), Exfoliating Toxins (EXft), Streptococcal Pyrogenic Exotoxin A, B and C (SPE A, B and C), Mouse Mammary Tumor Virus proteins (MMTV), Streptococcal M proteins, Clostridial Perfringens Enterotoxin (CPET), mycoplasma arthritis superantigens etc. For a review of superantigens and their properties see Kotzin et al 1993.

Wild-type and chimeric superantigens have also been mutated to have a reduced or no MHC class II binding and/or TCRVβ binding (Kappler et al WO 9314264; Kappler et al 1993; Blanco et al; Abrahmsén et al., WO9601650; Antonsson et al WO 9736932; Antonsson et al 1997). This type of superantigens becomes less toxic. In case they completely lack ability to bind to MHC class II or to TCRVβ they no longer are functional superantigens because they then lose their T cell activating ability.

By mutating structurally similar wild-type superantigens it has been possible to construct chimeric functionally active superantigens (hybrid superantigens) (Lamphaer et al., 1996 and Antonsson et al WO 9736932).

It has been discovered that activation and subsequent cell lysis can occur in a MHC class II independent manner in case the wild-type superantigen was conjugated with a target-seeking moiety capable of binding to a cell surface structure (Dohlsten et al WO9201470). This novel effector mechanism has been termed superantigen antibody dependent cell-mediated cytolysis (=SADCC). It includes the analogous mechanisms for targeting moieties other than antibodies (Abrahmsén et al., WO9601650; Antonsson et al WO 9736932).

Accordingly the superantigen concept of today encompasses any compound (preferably of polypeptide structure) that without intracellular processing is capable of binding to a cell surface structure (target structure) and to one or more polymorphic TCR chains, in particular the Vβ chain, thereby activating a subset of T cells expressing the specific TCR chain involved in the binding. The T cells then become cytotoxic and direct their cytotoxicity against cells carrying the surface structure (target structure, target cells). The definition of superantigen (SAG) as used in the context of he invention and if not otherwise specified thus will encompass conjugates between a targeting moiety and a free superantigen as discussed above for SADCC.

By the term superantigen is contemplated, if not otherwise specified, only functional superantigens.

A free superantigen (Sag) is a wild-type, possibly mutated or otherwise modified, superantigen that is not conjugated to a targeting moiety or to an immune modulator. The MHC class II binding ability of free superantigens is an inherent targeting property. Since free superantigens lack conjugated targeting moieties they will only exert SDCC.

A conjugated superantigen is a conjugate between a free superantigen and a targeting moiety or an immune modulator. A conjugated superantigen exerts either or both of SDCC and SADCC.

An immune modulator (IM) is a compound capable of regulating the immune system. In the context of the invention superantigens are treated separately and are not included when the term immune modulator is used. An immune modulator often has an inherent targeting ability, such as for a corresponding lymphocyte receptor. Unless otherwise specified, an immune modulator is in un-conjugated form.

A targeting moiety (T) is a moiety that is capable of binding to a cell surface structure and/or a tissue structure.

A conjugate is composed of two or more moieties Sag, IM, T etc that are linked to each other covalently.

By soluble forms of active ingredients means forms that are soluble in body derived fluids such as serum and plasma.

BACKGROUND ART

Therapeutic Use of Superantigens

Non-conjugated wild-type and mutated superantigens have been suggested for therapy with curative effect presumably being accomplished through an activation of the immune system, either locally at Class II expressing cells associated with the disease to be treated or as a systemic activation (Kalland et al WO9104053; Terman et al WO9110680 and WO9324136; Antonsson et al WO 9736932; and Newell et al 1991). Due to the extreme toxicity of wild-type superantigens this approach, with respect to cancer treatment, should only be applicable to a very minor fraction of all cancers.

It has also been suggested to use superantigens conjugated to target-seeking moieties (Dohlsten et al WO9201470; Abrahmsén et al WO9601650, Antonsson et al WO 9736932 and Ochi et al 1993), all three publications being incorporated by reference).

In connection with studies on prevention of superantigen induced down-regulation of T cell mediated cytotoxic activity by IL-2 in vivo it has been speculated that it should be beneficial to coadminister IL-2 with unconjugated wild-type superantigens and wild-type superantigens conjugated to antibodies (Belfrage Thesis Augusti/September 1996; Belfrage et al 1994; Belfrage et al 1995; Belfrage et al 1997a; Belfrage et al 1997b (wild-type superantigens))

It has also been suggested that cell membrane anchored CD80 has a role in superantigen activation of T cells in the absence of MHC class II antigens (Lando et al 1993 and 1996).

Figure 4:
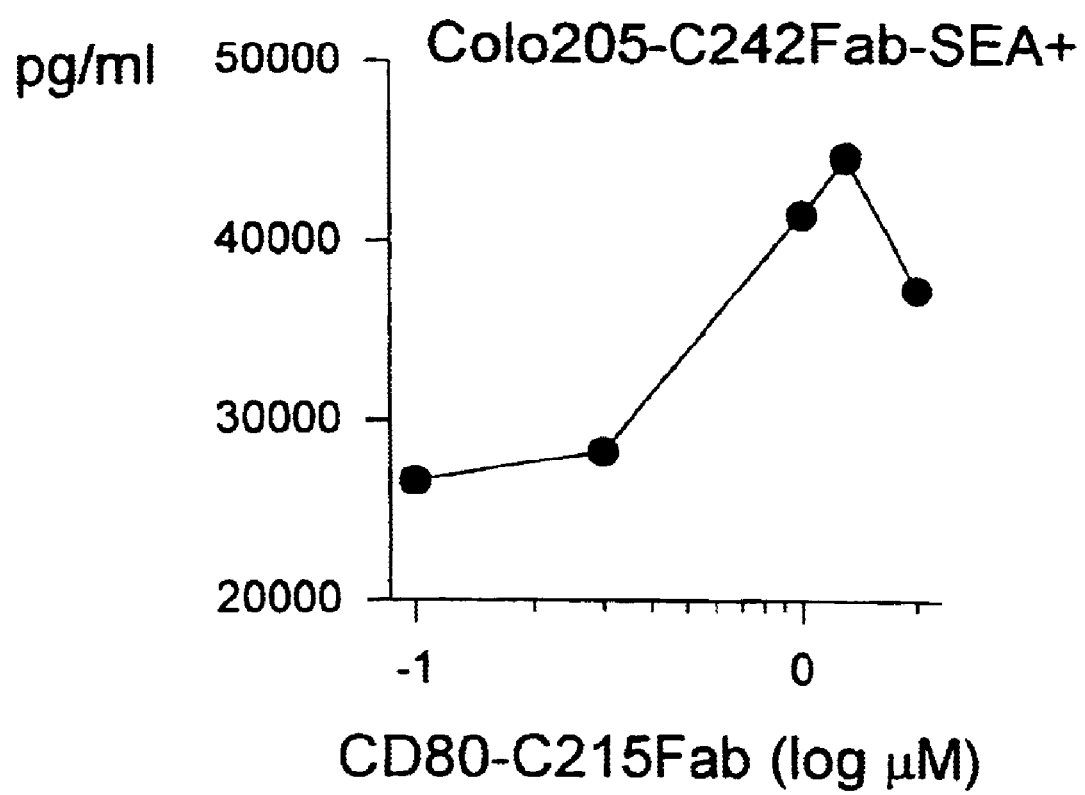

FIG. 4 in Lando et al 1996 shows an experiment in which the ability of superantigen conjugated to an antibody alone or in combination with IL-2 to induce proliferation of resting human T cells was analyzed. In this 4-day experiment the conjugated superantigen was presented on parent CHO-cell and CHO-cells transfected to express Class II or C215 or Class II plus C215. The effect of IL-2 was insignificant.

Kappler et al (WO9314634) have suggested non-conjugated wild-type SEB mutated to have lost its Vβ or MHC Class II binding ability (in the context of vaccines and as an agent to neutralize toxic effects of superantigens). Abrahmséet al (WO9601650) have suggested cancer therapy with conjugated superantigens having a modified, preferably decreased, ability to bind to Class II antigens. Antonsson et al (WO 9736932) has suggested therapy with chimeric superantigens and superantigens with reduced seroreactivity (see also Abrahmséet al). Mutations as described by Abrahmsén et al (WO9601650) and Antonsson et al (WO 9736932) will implicate superantigens with a lowered systemic toxicity, lowered immunogenicity and/or lowered seroreactivity in the mammal to be treated.

Therapy with administration of nucleic acids encoding wild-type superantigens have been suggested (Terman et al WO9110680; WO9324136) and Dow et al WO9636366). Dow et al go further on and suggest coadministration of a nucleic acid encoding a cytokine or a chemokine with a nucleic acid encoding a superantigen. Without enabling experimental support, WO9636366 also suggests constructs in form of a biscistronic gene construct in which one cistron contains the gene coding for the superantigen and the other cistron contains the gene coding for a cytokine or a chemokine.

Without enabling experimental support Pouletty P (Sangstat, EP510949) has speculated that conjugates between targeting moieties, such as IL-2, and wild-type superantigens might be useful for inactivating cells expressing the IL-2 receptor.

BACKGROUND ART

Therapeutic Use of Immune Modulators in Combination With Antibodies Specific to Cells That Are to be Inactivated It previously has been suggested to conjugate antibodies with biological response modifiers, for instance a chemokine or a cytokine, such as interleukin-2 (Fell et al EP 439095; Rosenblum et al EP 396387, Pancook et al 1996; and Becker et al 1996).

The Problem the Present Invention Sets Out to Solve

The present invention sets out to provide improvements in relation to superantigen therapy involving activation of the immune system in order to inactivate undesired target cells in a mammal to be treated. In particular the improvements relate to: 1. extending the activation period locally, for instance in a tumour, during a first treatment cycle; 2) counteracting the appearance of hyporesponsiveness due to the tendency of activated T cells to escape into anergy; 3) facilitating MHC class II independent T cell activation in the tumor area; and 4) broadening the therapeutic window for cytolysis via superantigen activation. It has now been discovered that these improvements wholly or partly may be accomplished provided that the administration of the superantigen (SAG) is combined with the administration of an immune modulator in soluble form, at least one of the superantigen and the immune modulator being in form of a conjugate with a moiety having targeting properties for the cell to be inactivated.

The First Major Aspect of the Invention: A Method of Inactivating Target Cells The first aspect of the invention covers both therapy and assays in vitro and is a method for inactivating undesired target cells in the presence of T cells by bringing the two types of cells in contact with a superantigen (SAG), in particular a superantigen that activates T cells through binding to TCRVβ, in the presence of an immune modulator (IM) that is not a superantigen (Sag). In its broadest aspect the method is characterized in that at least one of the superantigen and the immune modulator is in form of a conjugate with a moiety (T) having targeting properties for the cell to be inactivated. In a subaspect the method is characterized in that a. the superantigen (SAG) and the immune modulator is used in form of a triple conjugate comprising a superantigen (Sag), a targeting moiety (T) for the target cells and an immune modulator (IM) (T, IM, Sag-conjugate);

b. the superantigen (SAG) is used in form of a dual conjugate between a superantigen (Sag) and a targeting moiety (T) for the target cells in combination with a dual conjugate between an immune modulator (IM) and a targeting moiety (T') for the target cells (T, Sag-conjugate+T', IM-conjugate);

c. the superantigen (SAG) is used in form of a dual conjugate between a superantigen (Sag) and a targeting moiety (T) for the target cells and the immune modulator (IM) is used in free form, i.e. not conjugated to a targeting moiety for the target cells (T, Sag-conjugate+IM);

d. the superantigen (SAG) is used in free form (Sag) and the immune modulator is used in conjugate form, i.e. a dual conjugate between the immune modulator (IM) and the superantigen (Sag) (Sag+T, IM-conjugate); and e. the superantigen (SAG) and the immune modulator is used in form of a dual conjugate between a superantigen (Sag) and an immune modulator (IM) (Sag, IM-conjugate);

The superantigen and the immune modulator may be targeted to the same type of cells, for instance to identical or crossreacting structures/epitopes or to different type of cells within the same tissue. Targeting may be for normal cells or diseased cells associated with one and the same tissue. Either or both of the superantigen and the immune modulator may be targeted with one or several antibodies.

The Diseases to be Treated by the Method of the Invention

The diseases to be treated are in principle the same as those previously suggested for superantigens. See for instance under headings "Background . . . " above. Illustrative examples are cancers, autoimmune diseases, parasitic infestations, viral infections and other diseases associated with cells that on their surface express MHC class II antigens and/or other structures that are specific for respective disease and bind to the target-seeking moiety incorporated in the superantigen in accordance with the inventive concept (formula I). Also bacterial infections may be combated by the use of the invention.

Important cancer forms in the context of the invention are: melanomas, carcinomas, hematopoetic neoplasias and fibrosarcomas and includes specific forms such as squamous cell carcinoma, breast cancers, head and neck carcinomas, thyroid carcinomas, soft tissue carcinomas, bone sarcomas, testicular cancer, prostatic cancer, ovarian cancers, bladder cancers, skin cancers, brain cancers, angiosarcomas, hemangiosarcomas, mast cell tumors, primary hepatic cancers, lung cancers, cervix cancers, renal cell carcinomas, leukemias and lymphomas. Included are any type of malignant or benign tumors as well as multi-drug resistant cancers, metastatic cancers, various forms of chemically or virally (herpes, SV40, HIV etc) induced cancers.

The Second Major Aspect of the Invention: Inventive Superantigen Conjugates

This aspect of the invention comprises conjugates complying with the formula $$(T)_x(Sag)_y(IM)_z \qquad \text{Formula I}$$

T is a targeting moiety, Sag corresponds to a free superantigen and IM is an immune modulator that is not a superantigen. T, Sag and IM are linked together via organic linkers B that may be different or equal within one and the same conjugate molecule or substance. Conjugates according to formula I encompass chemical conjugates as well as recombinantly produced conjugates (fusion proteins). x, y and z are integers that typically are selected among 0–10, such as 0–5, and represent the number of moieties T, Sag and IM, respectively, in a given conjugate molecule, with the provision that y>0 and also one or both of x and z>0. Chemical conjugates are normally conjugate substances containing a mixture of different conjugate molecules. Accordingly in chemical conjugate substances x, y and z may also be non-integers within the range 0–10, such as within the range 0–5.

In a first subaspect of formula I, Sag and IM and T are present in the conjugate (x and y and z>0; T, Sag, IM-conjugates). x, y, and z are typically integers 1–3, with preference for 1–2. Typical relations between x, y and z are: x=y=z; x=y=0.5z; x=0.5y=0.5z; and x=0.5y=z.

In a second subaspect of conjugates according to formula I, the targeting moiety is absent (IM, Sag-conjugates, x=0). y and z typically are integers 1–3. Preferred relations between x and y are: x=y; x=0.5y, 0.5x=y; x=1/3y and 1/3x=y.

In both subaspects integers or relations primarily refer to fusion proteins in which the targeting moiety may be a protein containing 1, 2, 3 or 4 polypeptide chains and in which there are one T in each conjugate molecule.

Formula I for conjugates according to the second subaspect reduces to:

$$(Sag)_y(IM)_z \qquad \text{Formula II}$$

This type of conjugates are primarily adapted to the treatment of diseases associated with cells expressing MHC class II antigens, in particular class II expressing cancers, such as cancers of the hematopoetic system, and certain autoimmune diseases, viral infections and parasitic infestations, but also with diseases associated with cell membrane anchored receptors for the immune modulator, for instance T cell lymphoma expressing for instance the IL-2 receptor.

A. The Immune Modulator IM in Formula I

IM stands for an immune modulator that is not a free or conjugated superantigen.

The immune modulator may be a cytokine or a chemokine. Illustrative cytokines are granulocyte macrophage colony stimulating factor (GM-CSF), tumor necrosis factor α or β (TNFα or TNFβ), macrophage colony stimulating factor (M-CSF), granulocyte stimulating factor (G-CSF), IL-1, IL-2, IL-4, IL-6, IL-7, IL-12, IL-15, IL-18 and IGF. Illustrative chemokines are C5a, IL-8, monocyte chemotactic protein 1alpha (MIP1alpha) or monocyte chemotactic protein 1β (MIP1β), monocyte chemoattractant protein 1 (MCP-1), monocytic chemoattractant protein 2 (MCP-2), monocytic chemoattractant protein 3 (MCP-3), platelet activating factor (PAFR), N-formyl-methionyl-leucyl-phenylalanine (FMLPR), leukotriene $B_4$ ($LTB_4R$), gastrin releasing peptide (GRP), RANTES, eotaxin, lymphotactin, IP10, I-309, ENA78, GCP-2, NAP-2, MGSA/gro, DC-CK1, Flt3L (ectopic domain), fractalkin, PF-4 etc.

Another type of immune modulators are those derived from cell membrane anchored receptor/ligand pairs involved in modulation of a triggered immune response, such as costimulation (for instance lymphocyte surface bound receptors and corresponding cell bound ligands). Illustrative examples are members selected from the pairs CD40L/CD40, 4-BB1/4-BB1L, CD28/B7, CTLA-4/B7 etc. B7 includes variants such as CD80 and CD86 with preference for the former. Preferred forms are soluble, contain the extracellular part (ectopic domain) and are devoid of the intracellular and membrane anchored parts.

Particularly preferred immune modulators are capable of potentiating the effects of superantigens in vivo, for instance by counteracting escape of superantigen activated T-cells into anergy. Typical appropriate cell bound receptors/ligands are CD28/B7 including analogues and fragments as defined above. Typical cytokines of this group are IL-2, as being the main downstream effector of CD28/B7 signaling, and the IL-2 like cytokines IL-7 and IL-15. Among T cell surface associated receptor/ligand pairs the member not bound to the T cell to be activated is preferred to be incorporated in a conjugate according to the invention. For CD40L/CD40, 4-BB1/4-BB1L and CD28/B7 this means soluble forms CD40, 4-BB1L, and B7 with preferences as defined above. The experimental part of this text illustrates the immune modulator variants that at the priority date were found optimal in the invention.

Immune modulators should preferably be of the same species origin as the individual who is intended to be treated. Native immune modulators, such as cytokines and chemokines, often show a high systemic toxicity and a relatively short half life in mammals. The literature is extensive on how to modify immune modulators to an increased stability relative to oxidation, a longer in vivo half life, a lower toxicity, an improved refolding when produced by recombinant techniques etc. For instance U.S. Pat. No. 5,229,109 (Grimm et al) describes low toxicity analogues of IL-2 having a reduced affinity for the high affinity IL-2 receptor (IL-2R) by being deficient in binding to the p55 α subunit of the receptor. The analogues are primarily prepared by mutating the codon for an amino acid in position 33–46 in IL-2 (for instance Arg38Ala and Phe42Lys or Phe42Ala). The Asp20Lys mutant has 100–500 fold reduced affinity for the p75/β-chain of the IL-2 receptor without affecting binding to p55 (Collins et al 1988). Other mutations, e.g. Asp20Ser are less severe (Berndt et al 1994). Studies on murine IL-2 indicates that Asp84 and Asp88 of human IL-2 are also implicated in p75 binding (Zurawski et al 1993). This is supported by modelling of the binding between human IL-2 and its receptor (Bamborough et al 1994). The expected reduction in affinity of these mutations is Asp20>Asp88>Asp84.

Combining the mutations in Arg38 and Phe42 with mutations in position 88 and 20 would result in a still lower affinity for IL-2R. Another potent and at the priority date preferred IL-2 mutation is Thr51Pro that gives an IL-2 analogue with a lowered rate of cell internalization and a prolonged duration of its immune modulating effect (Chang et al 1996).

The numbering of amino acid positions is according to Taniguchi et al 1983.

The publications by Grimm et al; Collins et al 1988; Berndt et al 1994; Zurawski et al 1993; Bamborough et al 1994; Chang et al 1996; and Taniguchi et al 1983 are incorporated by reference.

The use of cytokine and chemokine analogues with a reduced affinity for their normal receptors in conjugates as described above will strengthen their targeting to the preselected target cell. It is conceivable that cytokines and chemokines mutated to show a reduced rate of cell internalization upon binding to their respective cell receptor and incorporated into a conjugate according to formula I will result in a prolonged superantigen activity compared to corresponding conjugates with the native form of the immune modulator.

The term immune modulator (IM) thus encompasses any modified form, for instance any mutated form, that is capable of agonizing or antagonizing the effects of the corresponding native form of the immune modulator.

B. The Superantigen Part SAG in Formula I

Sag in formula I represents a superantigen as defined for free superantigens and under heading "Background . . . " above, i.e. wild-type superantigens possibly modified, for instance by mutation, a. to have a decreased ability to bind to MHC class II antigen compared to the corresponding wild type superantigen (see for instance in Abrahmsén et al (WO9601650);

b. to have a decreased seroreactivity in human sera compared to the corresponding wild-type superantigen (see for instance Abrahmsén et al (WO9601650) and Antonsson et al WO 9736932 and Antonsson et al 1997);

c. to have a decreased immunogenicity in humans compared to the corresponding wild-type superantigen (see for instance Antonsson et al WO 9736932 and Antonsson et al 1997);

d. to be a chimera between two or more analogous wild-type superantigens in which one region in one first wild-type superantigen has been replaced with the corresponding region in a second analogous superantigen. The region in question may be a region determining binding to TCRVβ, e.g. as defined for SEE/SEA and SEA/SEE chimeras (see for instance Antonsson et al WO 9736932; Antonsson et al 1997; and Lamphaer et al 1996).

Also other modifications/mutations that may be found appropriate are included, for instance to avoid undesired glycosylation when produced in eucaryotic cells.

Typical mutations for SEA/SEE-like superantigens at the priority were (numbering as used by Antonsson et al, 1997 and Antonsson et al WO 9736932):

a. decreased MHC class II binding: Asp227Ala (=SEAm9), Phe47Ala and/or Asp70Arg. The mutant Phe47Ala/Asp227Ala=SEAm23.

b. and d. chimeras between SEA and SEE, aimed at reducing seroreactivity in humans, while retaining SADCC capability of the corresponding conjugated superantigen: SEE with the following substitutions Gly20Arg, Thr21Asn, Gly24Ser, Lys27Arg.

The mutants used in the experimental part are SEA (Asp227Ala) =SEAm9, SEA(Phe47Ala/Asp227Ala)= SEAm23 and SEA(Phe47Ala/Asn102Q/Asn149Asp/ Thr218Val/Asp227Ala)=SEAm57. At the priority filing preferred superantigens were selected among 1. superantigens (Sag) that exhibit two MHC class II binding sites (for instance staphylococcal enterotoxins A and E),
2. superantigens (Sag) that in their unmutated form required Zn-ion for optimal binding to MHC class II (for instance SEA, SEE and SEH),
3. Staphylococcal enterotoxins.

A Sag molecule that is to be incorporated into a conjugate according to the invention does not need to be a functional superantigen, the main issue being that the final conjugate is so by exerting either or both of SADCC and SDCC as outlined above.

C. Targeting moiety T in formula I

T can in principle be any structure that is able to bind to a cell surface structure, preferably a disease specific structure. The structure against which T is directed is usually different (a) from the polymorphic TCR chain epitope to which Sag binds, and (b) from the MHC class II epitopes to which Sag binds. The target-seeking moiety may be selected among interleukins (e.g. interleukin-2), hormones, antibodies including antigen binding fragments of antibodies, growth factors etc. See for instance Woodworth 1993 (hereby incorporated by reference).

The targeting moiety may thus be a protein containing 1, 2, 3 or 4 polypeptide chains.

At the priority date, it was preferred that T was an antibody (full length antibody, Fab, F(ab)$_2$, Fv, ScFv (single chain antibody), multiple single chain antibodies (ScFv)$_n$ and any other antigen binding antibody fragment), including any functionally active truncated form of the antibody forms mentioned above. Other variants are monospecific and bispecific. The antibody may in principle be directed towards any disease associated/specific cell surface structure, for instance structures linked to any of the cancer forms given above, with particular emphasis for antibody active fragments (such as Fab). Typically the antibody may be directed towards a colon and/or pancreatic specific epitope, for instance the so called C242 epitope (Lindholm et al WO9301303), a lung cancer specific epitope for instance the epitope for the 5T4 antibody (Stern et al WO8907947), a lymphoma specific epitope for instance on CD19, a melanoma specific epitope for example HMW-MAA, etc.

The term "antibody" comprises monoclonal as well as polyclonal variants, with preference for monoclonal preparations.

In case the target moiety is a Fab fragment the cysteine residues normally linking the heavy and light Fab chains together preferably have been replaced by an amino acid not permitting disulfide formation, for instance serine. See also Antonsson et al WO 9736932.

What has been said above also includes that T may be directed towards unique structures on more or less healthy cells that regulate or control the development of a disease.

D. The Linker B

The linker B may be selected as previously described (Dohlsten et al WO9201470; Abrahmsén et al WO9601650; and Antonsson et al WO 9736932), i.e. B shall preferably be hydrophilic and exhibit one or more structure(s) selected among amide, thioether, disulphide etc. The most prominent linkers are those obtained by recombinant techniques, i.e. conjugation takes place at the genomic level resulting in oligopeptide linkers. Typically oligopeptide linkers contain 1–30, such as 1–20, amino acid residues that preferably are selected so that the linker in total is hydrophilic. The linker residues thus preferably are selected among hydrophilic amino acid residues, such as Gln, Ser, Gly, Glu, Pro, His and Arg. Typical oligopeptide linkers comprise the tripeptide GlyGlyPro or the so called Q linker (Wootton et al 1989 hereby incorporated by reference) possibly modified with gly-pro at the amino terminal end.

E. Attachment Points for T, SAG and IM

Chemical conjugates will typically contain a mixture of conjugate molecules differing in linking positions. The conjugate substance will contain hetero- as well as homo-conjugates.

For recombinant conjugates (fusion proteins) the obtained conjugate substance will be uniform with respect to the linking position. For each individual subunit (T, Sag, IM) the amino terminal is fused to the carboxy terminal of another subunit or vice versa, preferably via an inserted oligopeptide bridge. The combinations in case the conjugate contains one each of T, IM, Sag will be T-IM-Sag, IM-T-Sag, Sag-IM-T, Sag-T-IM, T-Sag-IM, IM-Sag-T (the occurrence of linker structure of B is not shown). In case one or more of the subunits contains two or more polypeptide chains the number of possibilities increase. For T being an antibody Fab fragment the possibilities will be (the oligopeptide linkers B are not shown:

1. Sag-Fab (light chain)-IM Fab (heavy chain)
2. Fab (light chain) Sag-Fab (heavy chain)-IM
3. Sag-Fab (light chain) Fab (heavy chain)-IM
4. Fab (light chain)-IM Sag-Fab (heavy chain)
5. Sag-Fab (light chain) IM-Fab (heavy chain)
6. IM-Fab (light chain) Sag-Fab (heavy chain)
7. Fab (light chain)-Sag Fab (heavy chain)-IM
8. Fab (light chain)-IM Fab (heavy chain)-Sag In further variants the immune modulator and the superantigen may be fused in sequence at any end of any of the chains in the antibody.

At the priority date recombinant conjugates were preferred, with utmost preference for Fab fragments as targeting moiety and linking of the amino terminal of the free superantigen to the first constant domain of the heavy ($C_H1$) or light antibody chain and the immune modulator to the remaining carboxy terminal (valid for formulas I–IV).

For optimal production and function the fusion protein is expressed recombinantly as a two chain product in which the superantigen is fused C-terminally to the $C_H1$-domain of the antibody Fab fragment via a flexible hydrophilic amino acid linker of 3–11 residues. This linker may have the sequence Gly-Gly-Pro or Pro-Ala-Ser-Gly-Gly-Gly-Gly-Ala-Gly-Gly-Pro (SEQ ID NO: 19) or 4–9 residues based on SEQ ID NO: 19, with SEQ ID NO: 19 being preferred. The immune modulator moiety is fused C-terminally to the light chain via a hydrophilic and neutral or positively charged linker of 10–20 residues (linker Q). Preferably, linker Q may have the following sequences Gly-Pro-Arg-Gln-Ala-Asn-Glu-Leu-Pro-Gly-Ala-Pro-Ser-Gln-Glu-Glu-Arg (SEQ ID NO: 23), Gly-Pro-Arg-Gln-Ser-Asn-Glu-Thr-Pro-Gly-Ser-Pro-Ser-Gln-Glu-Glu-Arg (SEQ ID NO: 20), Gly-Pro-Arg-Gln-Ala-Lys-Thr-Leu-Pro-Gly-Ala-Pro-Ser-Gln-Thr-Thr-Arg (SEQ ID NO: 21) or Gly-Pro-Thr-Glu-Ala-Asp-Glu-Leu-Pro-Gly-Ala-Pro-Ser-Glu-Glu-Glu-Thr (SEQ ID NO: 22), with SEQ ID NO: 20 and 21 being most preferred (see Example 2 for more details).

The analogous combinations at the amino terminal or combination of attachments at the amino and carboxy terminals of the VH and VL domain were at this stage believed to result in active but less efficient conjugates.

F. Active Entities Not Complying With Formula But Used According to the Combinations a–e Above in the Inventive Method Free superantigens (Sag): See under heading "Definition". Typical Sags are given under the headings "Background" and "B. The superantigen part of Sag in formula I".

Unconjugated immune modulators: See under heading "Definition". In principle the same immune modulators as given under the heading "A. The immune modulator IM in formula I" can be used. Cytokines and chemokines are preferred with emphasis for IL-2 and IL-2-like cytokines.

Targeted immune modulators (T, IM-conjugates): These conjugates comply with the general formula $$(T')_x(IM')_z \qquad \text{Formula III}$$

in which T' and IM' are linked together by an organic linker B'. T', IM' and B' are selected among the same groups of compounds/structures as T, IM and B. x and z are defined in the same way as in formula I (y=0), with preference for one or two IM' per T' and conjugate molecule. The attachment points between T' and IM' are as defined for formula I. See also under heading "E. Attachment points . . . " in which the formulas 1–8 and comments thereto are applicable also to T, IM conjugates except that Sag is omitted. Conjugates of formula III can be manufactured according to known techniques, i.e. conventional chemical linking or recombinant techniques (fusion proteins), with preference for the latter (Fell et al EP 439095; Rosenblum et al EP 396387). Particularly important T, IM-conjugates comprise an IM'-moiety that has been modified, for instance mutated, to a reduced affinity and/or reduced rate of internalization as defined above.

Targeted superantigens (T, Sag-conjugates). These conjugates comply with the general formula $$(T'')_x(Sag'')_y \qquad \text{Formula IV}$$

in which T'' and Sag' are linked together by organic linkers B''. T'', Sag'' and B'' are selected among the same groups of compounds/structures as T, IM and B. x and y are defined in the same way as in formula I (z=0), with preference for one or two Sag'' per T'' and conjugate molecule. The attachment points between T'' and Sag'' are as defined for formula I. See also under heading "E. Attachment points . . . " in which the formulas 1–8 and comments thereto are applicable also to T, Sag conjugates except that IM is omitted from the formula. Conjugates of formula II can be manufactured according to known techniques, i.e. conventional chemical linking or recombinant techniques (fusion proteins), with preference for the former. See for instance Dohlsten et al WO9201470; Abrahmsén et al WO 9601650, Antonsson et al WO WO 9736932.

Third Major Aspect of the Invention: Conjugates Containing a Modified Immune Modulator These novel conjugates complies with the formula:

$$(T''')_x(Sag''')_y(IM''')_z \qquad \text{Formula V}$$

where T''' and Sag''' are selected among the same compounds as T and Sag for formula I. IM''' is an immune modulator that has been modified, for instance by mutation, to exhibit a lowered affinity to its cell membrane anchored receptor and/or a lowered rate of internalization via binding to its receptor (compared to corresponding native forms). IM'' is preferably a cytokine or a chemokine. See further under heading "A. The immune modulator IM in formula I". One important immune modulator for this aspect of the invention is modified IL-2. x, y and z are defined in the same way as in formula I.

In a first subaspect of conjugates according to formula V, T''', Sag''' and IM''' are always present (all x, y and z>0), i.e. T, Sag, IM-conjugates. x, y and z are typically integers 1–3, with preference for 1–2. Typical relations between x, y and z are: x=y=z; x=y=0.5z; x=0.5y=0.5z; and x=0.5y=z.

In a second subaspect of conjugates according to formula V, the superantigen moiety is absent (y=0), i.e. T, IM-conjugates. x and z are typically integers 1–3. Preferred relations between x and z are: x=z; x=0.5z, 0.5x=z; x=1/3z and 1/3x=z.

In both subaspects of conjugates according to formula V, the ranges given for integers and their interrelations primarily refer to fusion proteins in which the targeting moiety may be a protein containing 1, 2, 3 or 4 polypeptide chains and in which there are one T in each conjugate molecule. The attachment points in fusion proteins of formula V are the same as for corresponding fusion proteins complying with formula I. See also under heading "E. Attachment points . . . " in which the formulas 1–8 and comments thereto are applicable also to T, IM conjugates except that, for the second subaspect, Sag is omitted.

Manufacture of Conjugates Defined Above

The manufacture of conjugates may be carried out in principle according to two main routes:

1. Chemical linking of the individual subunits T, Sag and IM together. Each individual subunit or combination of them may have been produced by recombinant techniques.
2. Recombinant techniques directly providing a conjugate as defined in any of formulas given above.

The factual methods are well recognized for the average skilled worker and comprise a large number of variants.

Chemical linking typically utilizes functional groups (e.g. primary amino groups, carboxy groups, mercapto, carbohydrate groups) that typically are natively present in several positions of superantigens, proteinic immune modulators and proteinic targeting moieties. The techniques are well-known in the art.

The main host cell for large scale recombinant production of the inventive conjugates between a superantigen and an immune modulator (fused forms as well as non-conjugated forms) is *E. coli.* This host provides for in principle two routes: intracellular production and secretion. The latter variant is preferred because it offers purification of correctly folded proteins from the periplasma and from the culture medium. The above does not exclude that it is possible to produce active conjugates also in other host cells, e.g. eukaryotic cells, such as yeast or mammalian cells. Preliminary results have so far indicated that eukaryotic cells, such as mammalian cells, may be preferred for incorporating immune modulators interacting with CD28, for instance B7 and its analogues.

The Fourth Aspect of the Invention: Gene Constructs Encoding the Novel Inventive Conjugates A fourth aspect of the invention is a recombinant nucleic acid molecule, preferably DNA, such as cDNA, or RNA, encoding a superantigen and an immune modulator as defined above, with preference for IL-2, IL-7, IL-12, IL-15, IL-18, RANTES, ectopic domain of CD80, ectopic domain of CD86, 4-BB1L and Flt3L and their analogues as defined above. In this aspect of the invention, the nucleic acid typically should contain regulatory control sequences such as translation regulatory sequences, origin of replication, secretory signal sequences either for one or both of the immune modulator and the superantigen, etc that are compatible with the host cell in which the immune modulator and the superantigen are to be expressed. The region between the part sequences encoding the superantigen and the immune modulator may comprise a sequence encoding a ribosome entry sites such as in biscistronic gene constructs. The latter will allow separate expression of each polypeptide chain comprised within the conjugate. In case of multichain conjugate combinations containing IM, Sag, targeting moiety conjugate and the proper signal sequences, biscistronic constructs will facilitate folding and assembly to fully active conjugates with IM bound to one of the chains. This will be important for cases in which the targeting moiety is a two chain antibody molecule and at least one of the superantigen (Sag) and the immune modulator is fused to a terminal end of the antibody chain. See above.

Pharmaceutical Compositions, Dosage and Routes of Administration

A fourth aspect of the instant invention is a pharmaceutical composition containing the inventive combination of superantigen (Sag), targeting moiety (T) and immune modulator (IM). The characteristic feature of this aspect of the invention is that at least one of the superantigen and the immune modulator is in the form of a conjugate permitting targeting to cells that are to be inactivated as described above.

The compositions contemplated are known in the field, except that now they contain the inventive conjugate combination. In particular composition the combination may comprise:

a. a triple conjugate comprising a superantigen (Sag), a targeting moiety (T) for the target cells and an immune modulator (IM) (T, IM, Sag-conjugate);
b. two dual conjugates—one between a targeting antibody (T) and a superantigen and one between a targeting antibody (T') an immune modulator (i.e. T, Sag-conjugate+T', IM-conjugate). T and T' may be different or equal as regard to epitope specificity;
c. on dual conjugate between a superantigen (Sag) and a targeting moiety (T), and an immune modulator (IM) in free form (T, Sag-conjugate+IM);
d. one dual conjugate between an immune modulator (IM) and a targeting moiety (T), and a superantigen in free form (Sag) (T, IM-conjugate+Sag); or
e. a superantigen (Sag) and an immune modulator (IM) in form of a dual conjugate (Sag, IM-conjugate);

See further above in the context of the inventive methods. In case the compositions contain two active components (b–d above) the composition may allow for keeping the components apart up to the occasion for administration.

The compositions may be in the form of a lyophilized particulate material, a sterile or aseptically produced solution, a tablet, an ampoule etc. Vehicles such as water (preferably buffered to a physiologically acceptable pH value by for instance PBS) or other inert solid or liquid material may be present. In general terms the compositions are prepared by the conjugate, possibly in combination with an unconjugated active component, being mixed with, dissolved in, bound to, or otherwise combined with one or more water-soluble or water-insoluble aqueous or non-aqueous vehicles, if necessary together with suitable additives and adjuvants. It is imperative that the vehicles and conditions must not adversely affect the activity of active components as defined in a–e above.

Normally the superantigens (SAG) to be used in the invention will be sold and administered in predispensed dosages, each one containing an effective amount of SAG that, based on the result now presented, is believed to be within the range of 1 pg–50 mg. The exact dosage will vary from case to case depending on the patient's weight and age and pretiter of antibodies specific for the SAG used, route of administration, type of disease, target-seeking moiety, superantigen, linkage (-B-), immune modulator etc.

An important factor to account for in determining the dose for a a combination to be used in the inventive method is that superantigens and immune modulators exert optimal dose ranges. A too low dose will result in no or a suboptimal effect and a too high dose will give unacceptable side effects such as toxicity that may be lethal. Thus it has to be emphasized the broad range given above is an attempt to encompass all ranges possible for all variants of the inventive method. Thus, each specific combination according to the inventive method has a dose subrange within the range of 0.1 pg to 50 mg. This does not exclude that future developments and results may lead to dose levels outside this range.

The administration routes will be those commonly contemplated within the field, i.e. a target killing effective amount or therapeutically active amount of a superantigen-immune modulator combination according to the invention is brought into contact with the target cells. For the indications specified above this mostly means parenteral administration, such as injection or infusion (subcutaneously, intravenously, intraarterial, intramuscularly, intraperitoneal) to a mammal, such as a human being. The conjugate combination of the invention may be administered locally or systemically.

By the term "target killing effective amount" is contemplated that the amount is effective in activating and directing T cells to destroy target cells.

The preferred administration routes at the priority date are the same as contemplated for the superantigen conjugates according to Dohlsten et al WO9201470; Abrahmsén et al WO9601650 and Antonsson et al PCT/97/00537. This means 1–5 hours' intravenous infusion (preferably 4 hours) per day combined with a fever-reducing agent (paracetamol). The administration is to be repeated during some days, for instance 5–8 days, with care consideration taken for the risk of boostering antibodies directed towards the conjugate. Optimally, several cycles of therapy with each cycle containing treatment during one or more days followed by a rest period during one or more days, e.g. cycles with treatment and resting during 5 and 2 days, respectively.

The inventive compositions may be administered either as the main therapy or in preferred modes as adjuvant therapy in connection with surgery or with other drugs.

EXPERIMENTAL PART

Legends to the Figures

FIG. 1, FACS analysis of CHO-CD28 cells stained with CD80-C215Fab, CD80-C215Fab-SEAm57 or C215Fab-SEA followed by incubation with anti-mouse kappa chain mAb labeled with PE. The staining were done at 4° C. without any washes. Ordinate: mean channel.

Figure 2:
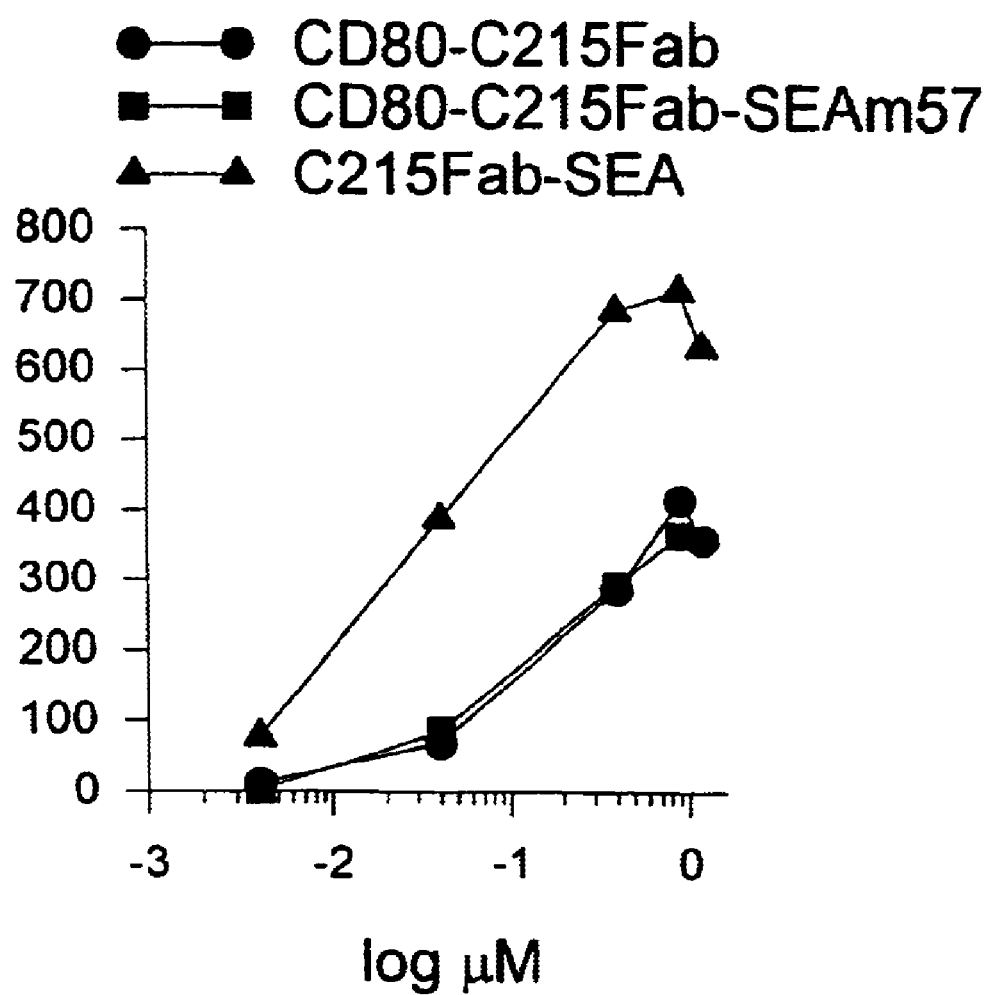

FIG. 2. FACS analysis of Colo205 cells stained with CD80-C215Fab, CD80-C215Fab-SEAm57 or C215Fab-SEA followed by incubation with anti-mouse kappa chain mAb labeled with PE. The staining were done at 4° C. with three washes between each staining step. Ordinate: mean channel. Abscissa: Effector (E) to Target cell (T) ratio.

Figure 3:
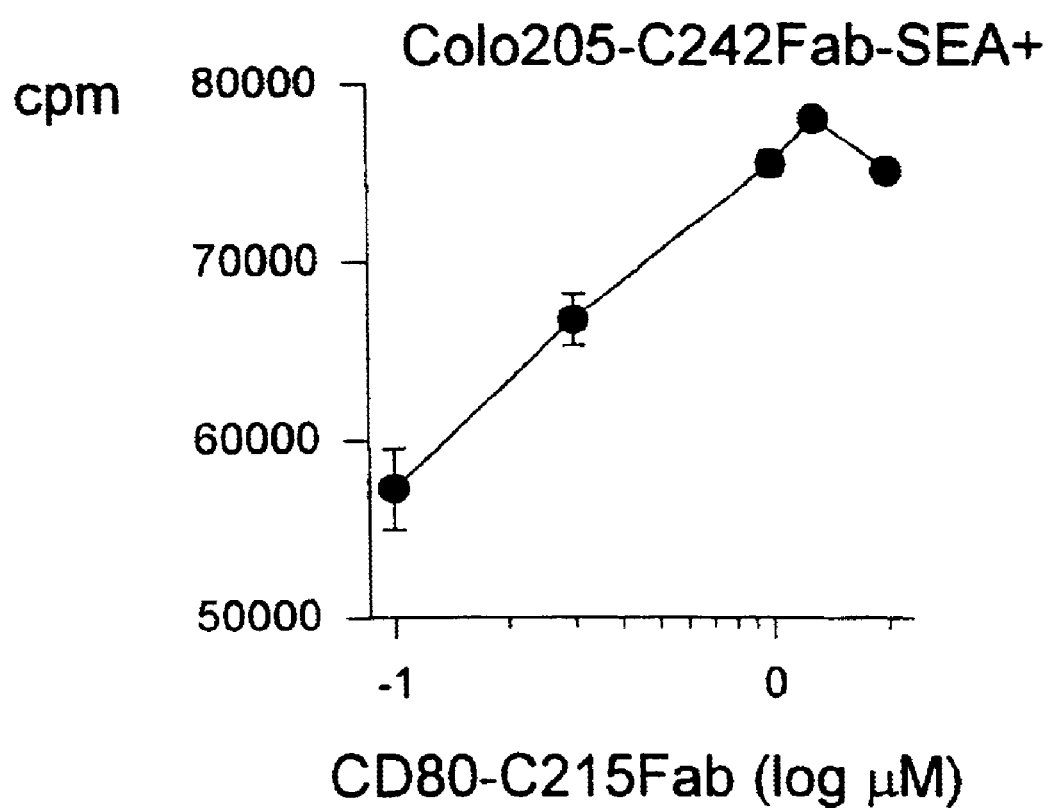

FIG. 3. Proliferation. T cells were incubated with Colo205 cells and 4 uM C242Fab-SEA and varying amounts of CD80-C215Fab for 4 days after which the incorporated $^3$H-thymidine was counted. The activity obtained without any CD80-C215Fab was 20039 cpm+/−1750.

FIG. 4. IL-2 production. T cells were incubated with Colo205 cells and 4 uM C242Fab-SEA and varying amounts of CD80-C215Fab for 4 days after which the supernatant was harvested and the amount IL-2 was determined. The amount IL-2 obtained without any CD80-C215Fab was 2849 pg/ml.

Figure 5:
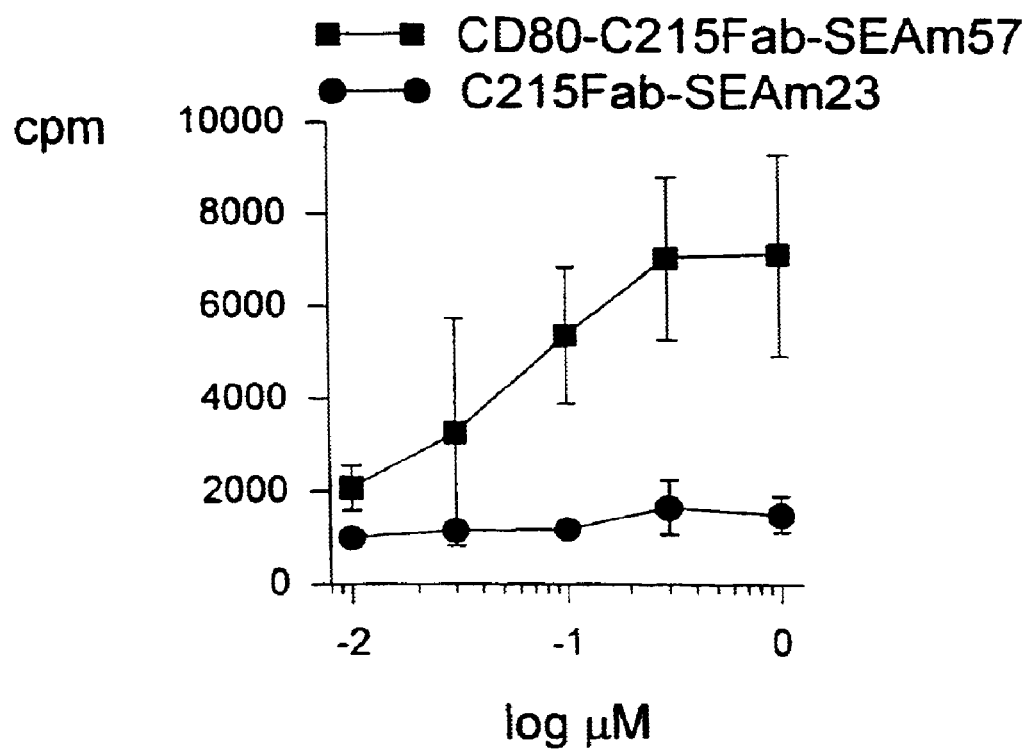

FIG. 5. Proliferation. T cells were incubated with Colo205 cells and varying amounts of CD80-C215Fab-SEAm57 or C215Fab-SEAm23 for 4 days after which the incorporated $^3$H-thymidine was counted.

Figure 6:
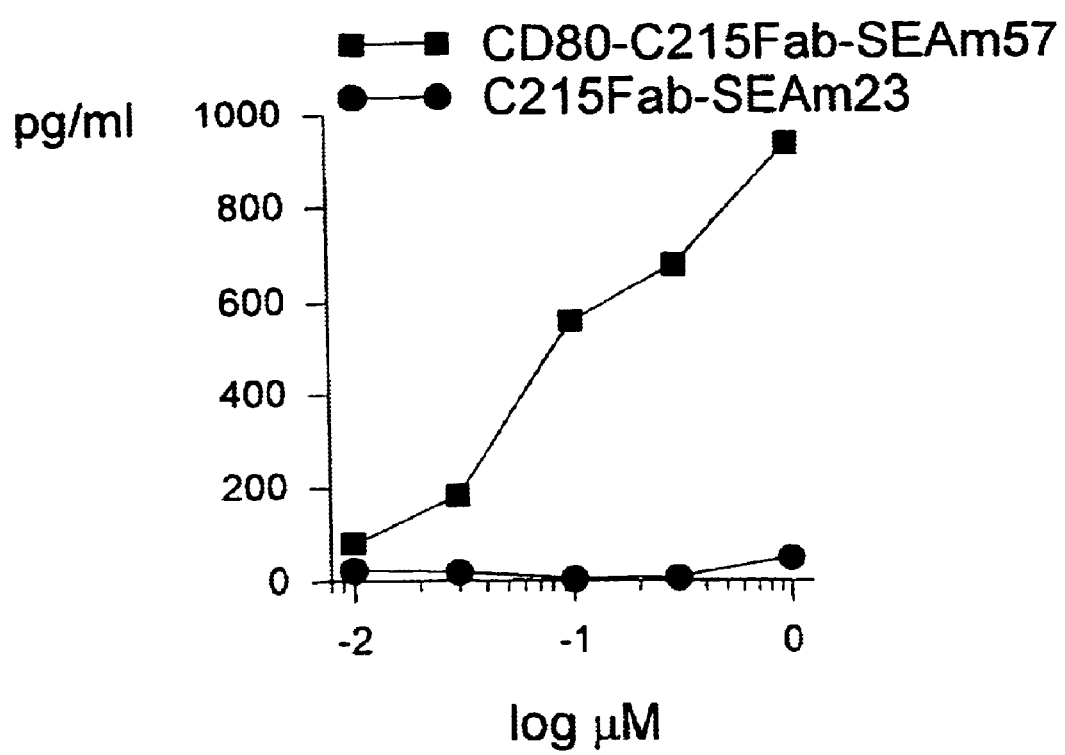

FIG. 6. IL-2 production. T cells were incubated with Colo205 cells and varying amounts of CD80-C215Fab-SEAm57 or C215Fab-SEAm23 for 4 days after which the supernatants were harvested and the IL-2 contend determined.

Figure 7:
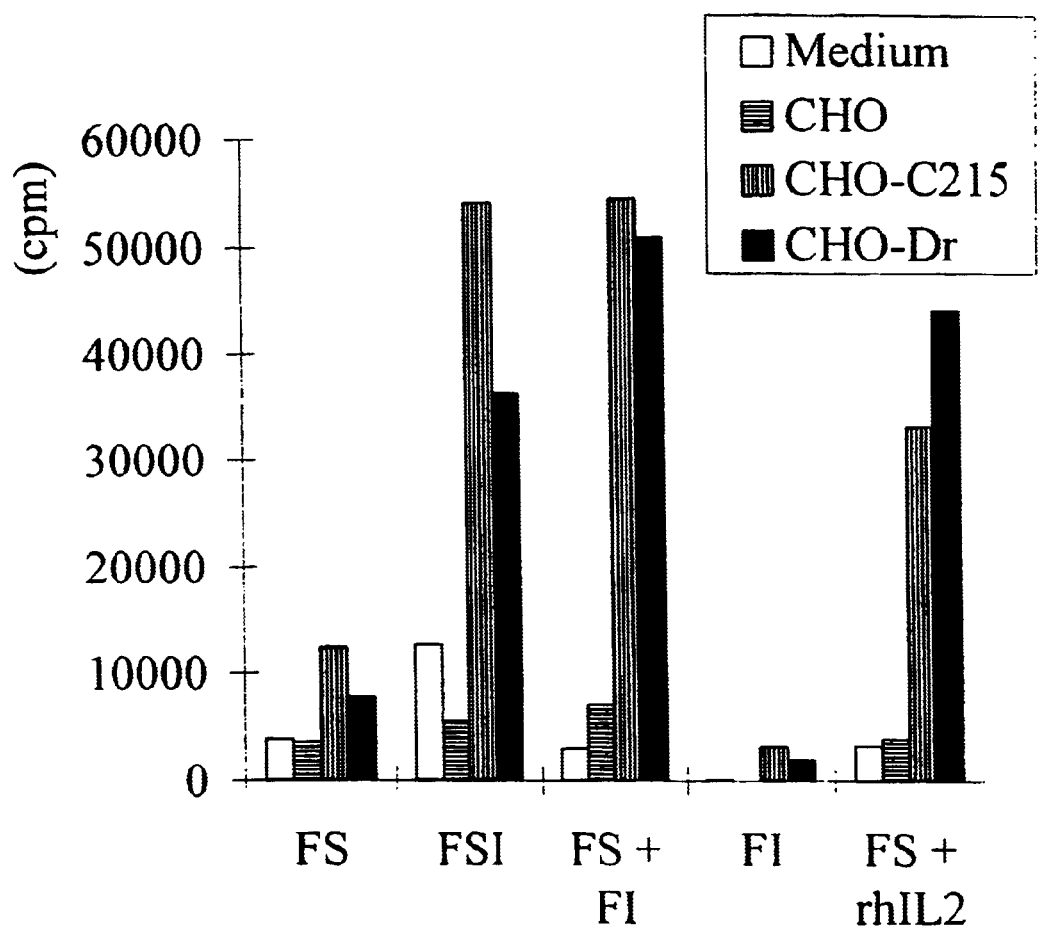

FIG. 7. Proliferative capacity of human blood T cells incubated for 7 days with the indicated proteins and irradiated, transfected CHO cells (for presentation of SEA). Ordinate: $^3$H-Thymidine incorporation (cpm)

Figure 8:
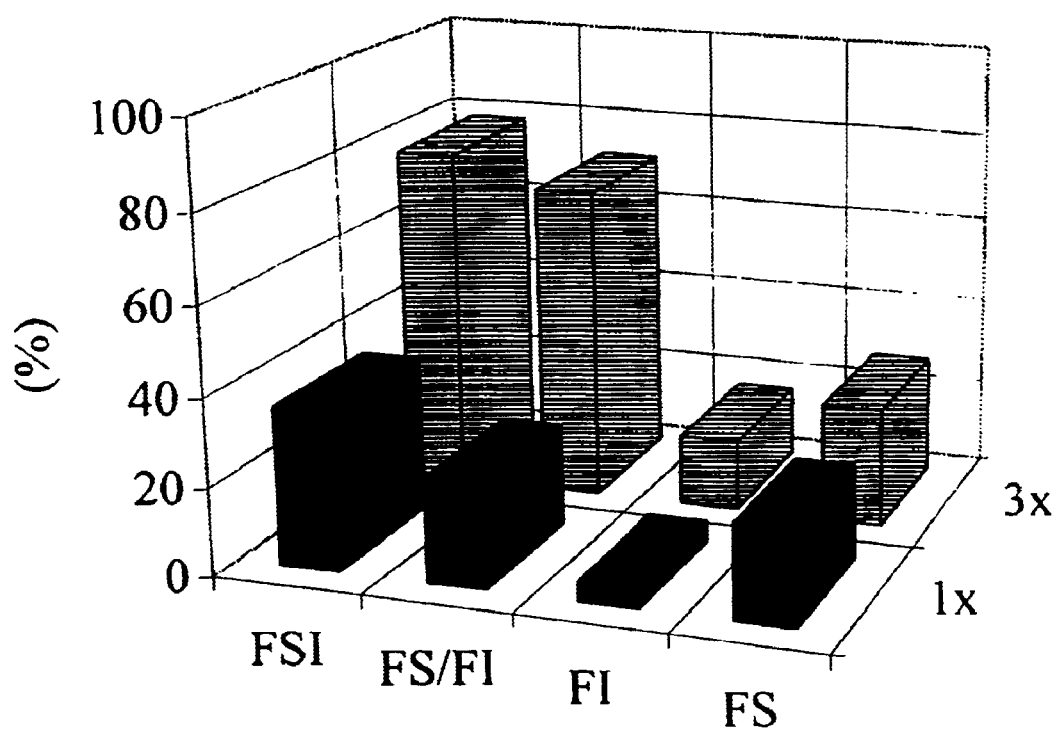

FIG. 8. Simultaneous administration of targeted SEA and IL2 leads to enhanced T cell activation in vivo. Cytotoxicity (expressed as percentage) against SEA-coated MHC class II$^+$ Raji cells of spleenocytes from mice treated with 1 or 3 injections of C215FabSEA (FS), C215Fab-Q-hIL2 (FI), combination of the two (FS+FI) or C215FabSEA-Q-hIL2 (FSI). Effector:target cell ratio was 30:1, and cytotoxicity was measured in a standard 4 hr $^{51}$Cr release assay FIG. 9. Therapy of day 5 B16-C215 tumors in C57Bl/6 mice with three injections (days 5, 6 and 7 after tumor inoculation) of C215FabSEA (FS), C215Fab-Q-hIL2 (FI), C215FabSEA+C215Fab-Q-hIL2 (FS+FI) or C215Fab-Q-hIL2 (FSI). Equimolar amounts of FabSEA and Fab-Q-hIL2 were used. Abscissa: amount of injected protein. Ordinate: tumor reduction expressed in percentage.

Figure 10:
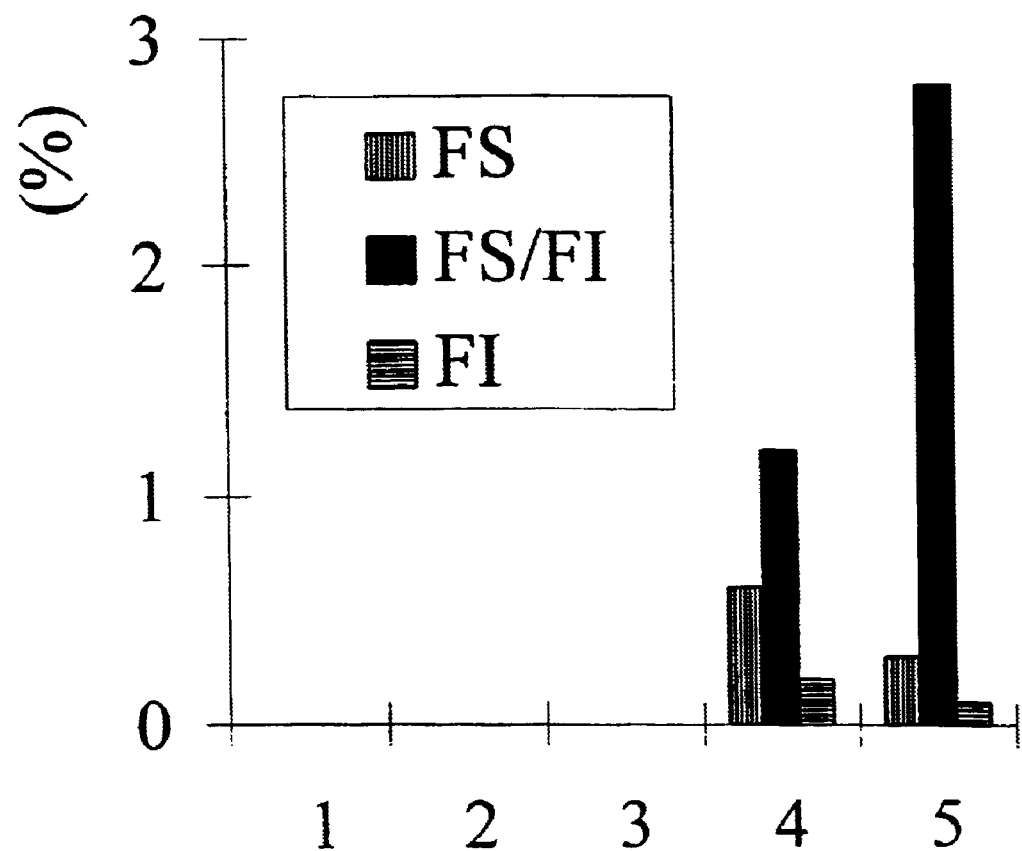

FIG. 10. Increased tumor infiltration of CD25$^+$ T cells following C215Fab-SEA (FS), C215Fab-Q-IL2 (FI) or C215FabSEA-Q-IL2 treatment. CD25-positive cells infiltrating the lung of mice carrying established B16-GA733 lung tumors were estimated byimmunohistochemistry. Ordinate: percentage of stained area. Abscissa: 1=PBS; 2=first injection; 3=second injection; 4=injection; 5=fourth injection.

Figure 11:
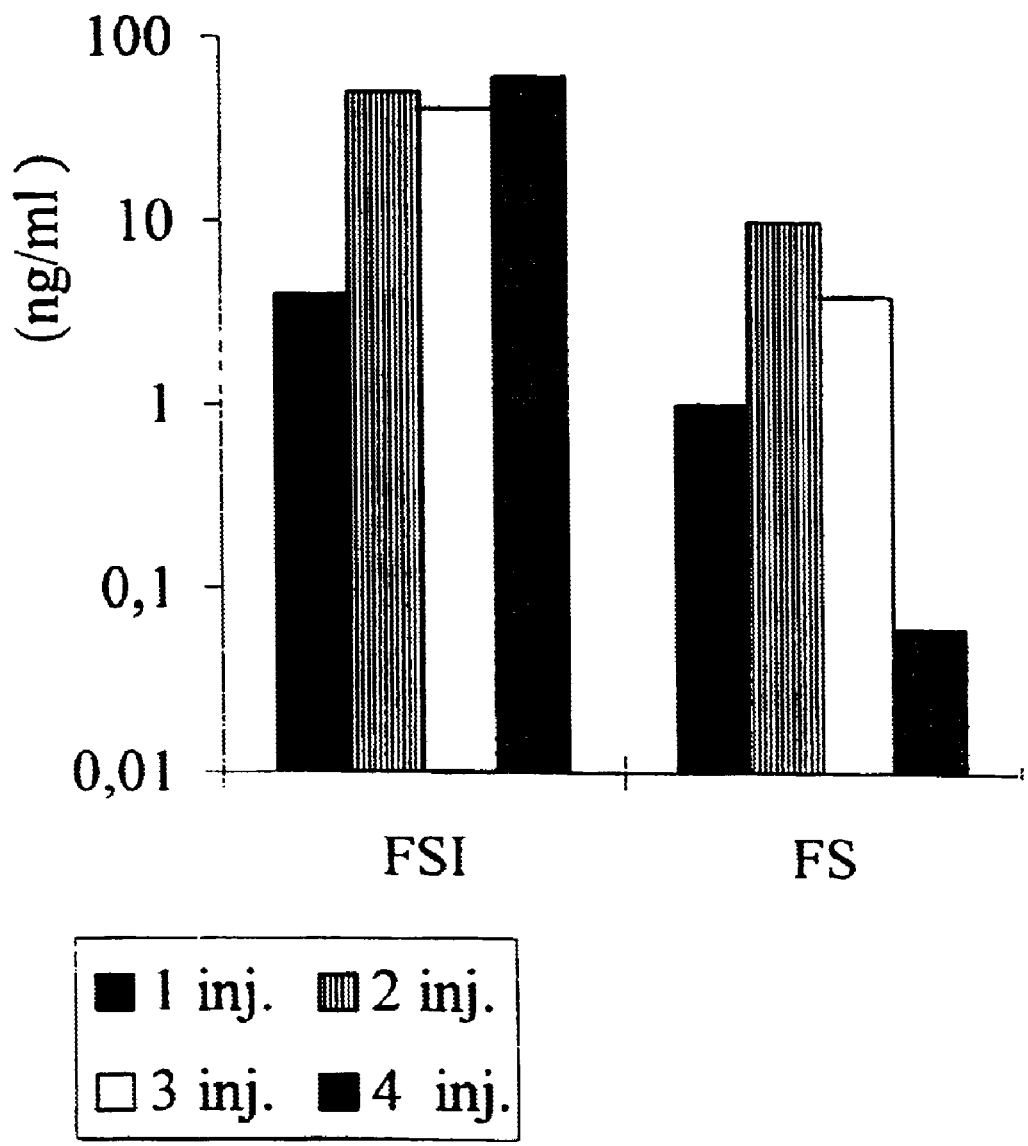

FIG. 11. Sustained levels of Interferon γ following up to four injections, once daily (37 mg/injection), of C215FabSEA-Q-hIL2 (FSI) (37 mg/). Blood was collected four hours after the last injection and the The interferon γ content (in the ordinate) was determined by ELISA measurement using recombinant murine Interferon γ (Pharmingen) as standard. A similar experiment was performed with equimolar amounts (30 mg/injection) of C215FabSEA (FS).

Figure 12:
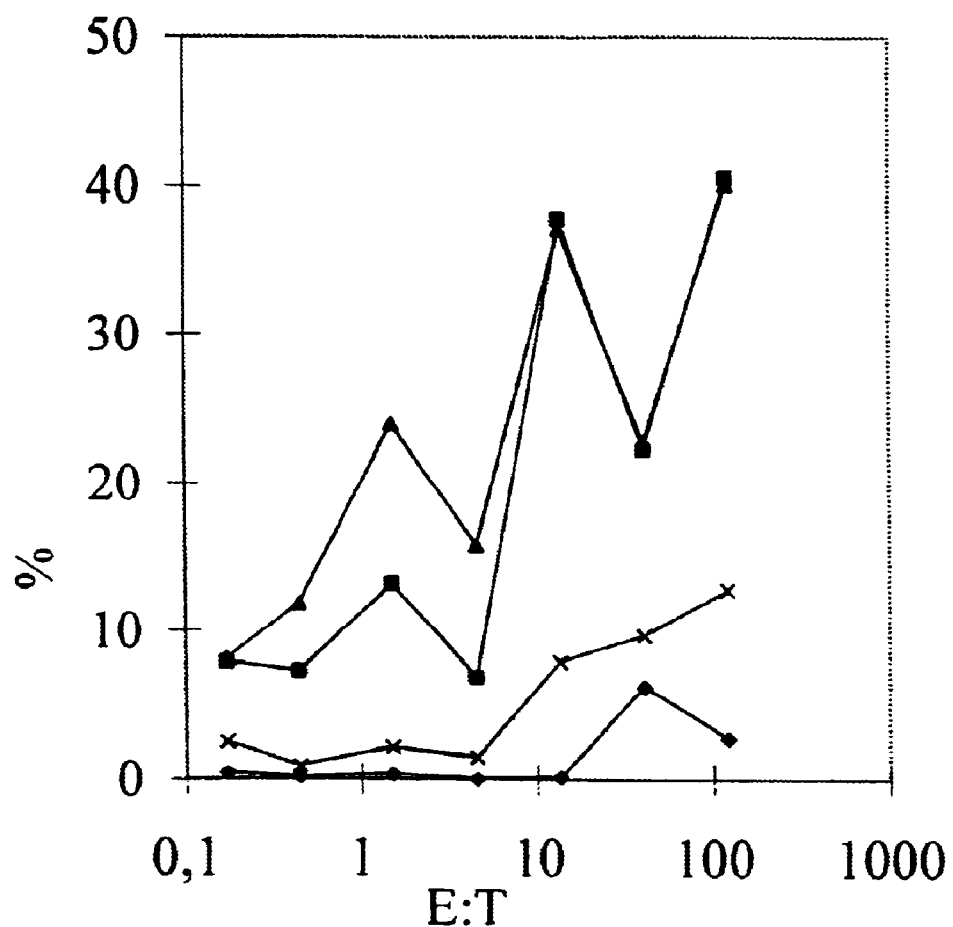

FIG. 12. Cytotoxicity (expressed as percentage in the ordinate) against SEA-coated MHC class II$^+$ Raji cells of splenocytes from mice treated with PBS or 1, 4 or 6 injections of C215FabSEA$_{D227A}$-Q-hIL2 (=FSm9-IL2). Cytotoxicity was measured in a standard 4 hr $^{51}$Cr release assay. PBS is used as negative control.

Figure 13:
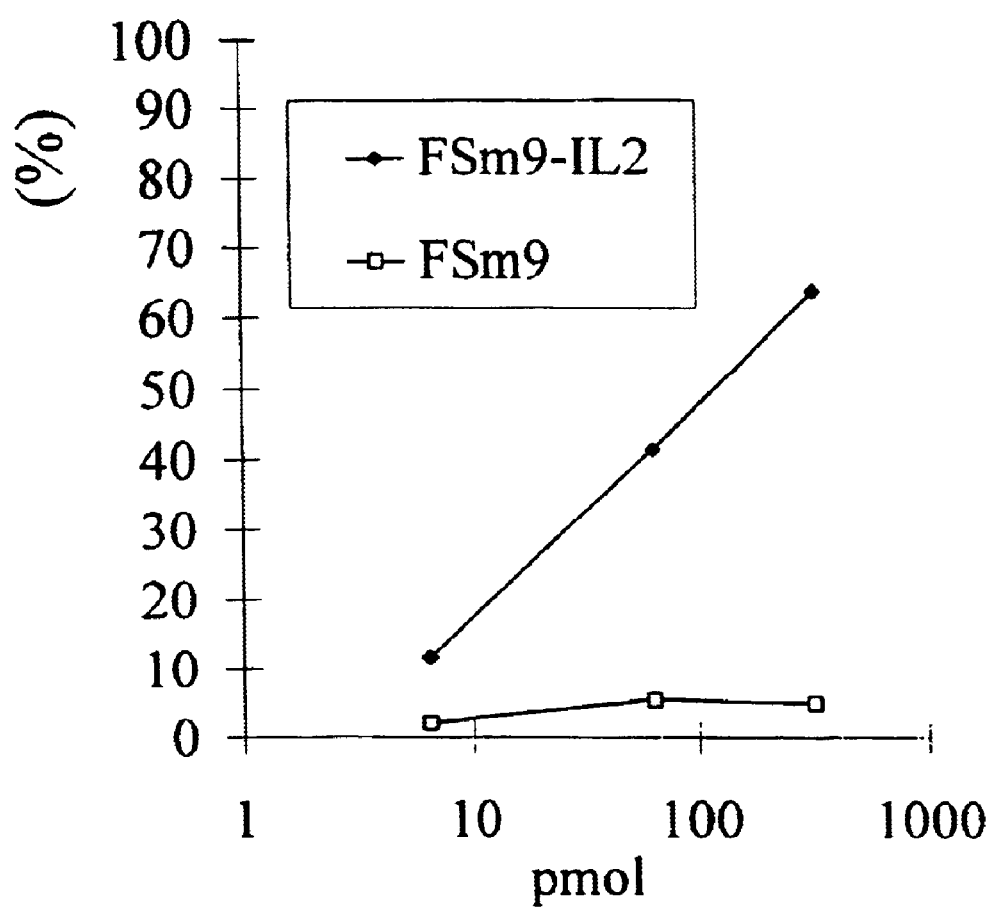

FIG. 13. Therapy of day 3 B16-C215 tumors in C57 Bl/6 mice following treatment with 8 injections C215FabSEA$_{D227A}$ (=FSm9) or C215FabSEA$_{D227A}$-Q-hIL2 (=FSm9-IL2). Treatment given daily for 8 consecutive days. On day 21 animals were sacrificed, and lung metastases counted. Ordinate: tumor reduction expressed in percentage.

Figure 14:
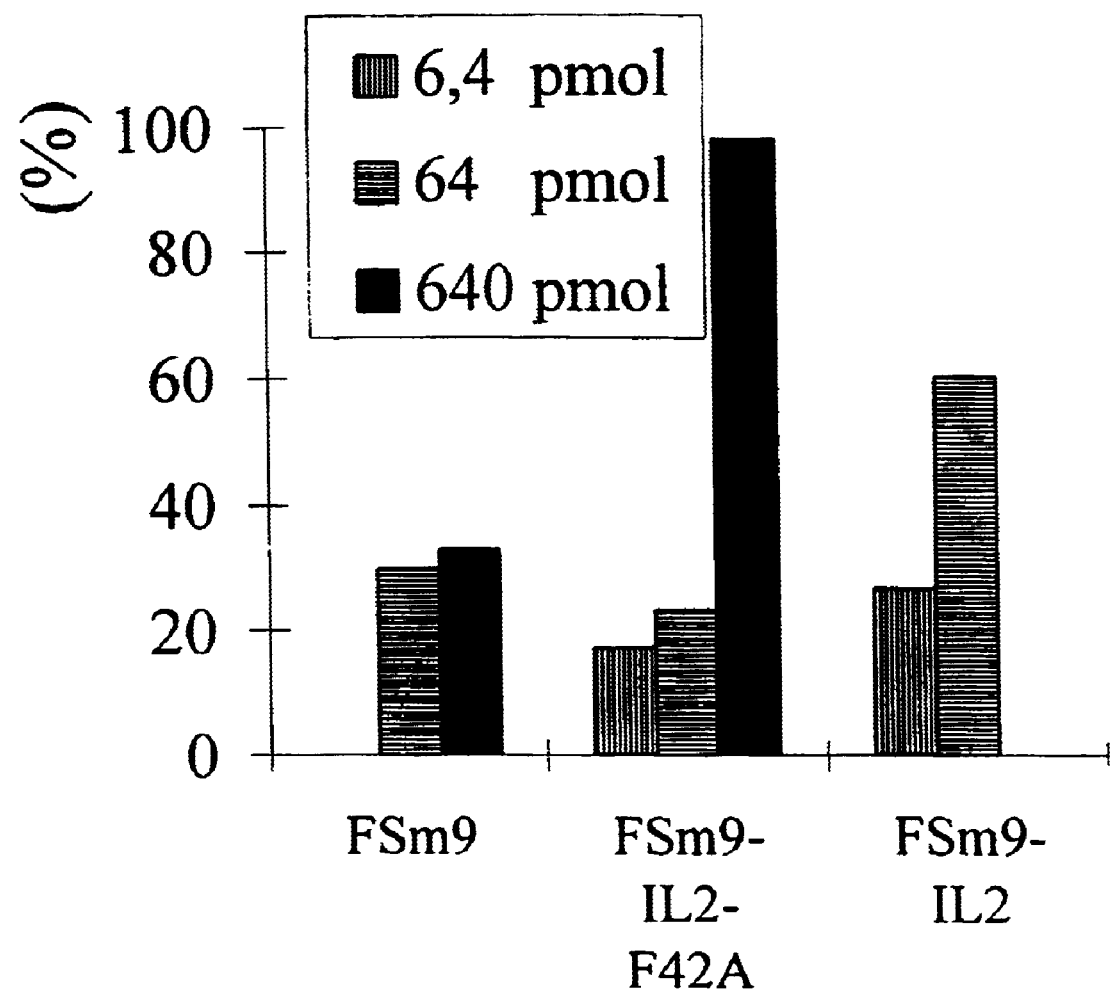

FIG. 14. Therapy of day 3 B16-C215 tumors in Vb3 TCR transgenic mice following treatment with 8 injections of C215FabSEA$_{D227A}$-Q-hIL2$_{F42A}$ (=FSm9-IL2 (F42A)),, C215FabSEA$_{D227A}$-Q-hIL2 (=FSm9-IL2), or C215FabSEA$_{D227A}$ (=FSm9-IL2). Treatment was given daily for 8 consecutive days. On day 21 animals were sacrificed, and lung metastases counted. Ordinate: tumor reduction expressed in percentage.

Figure 15:
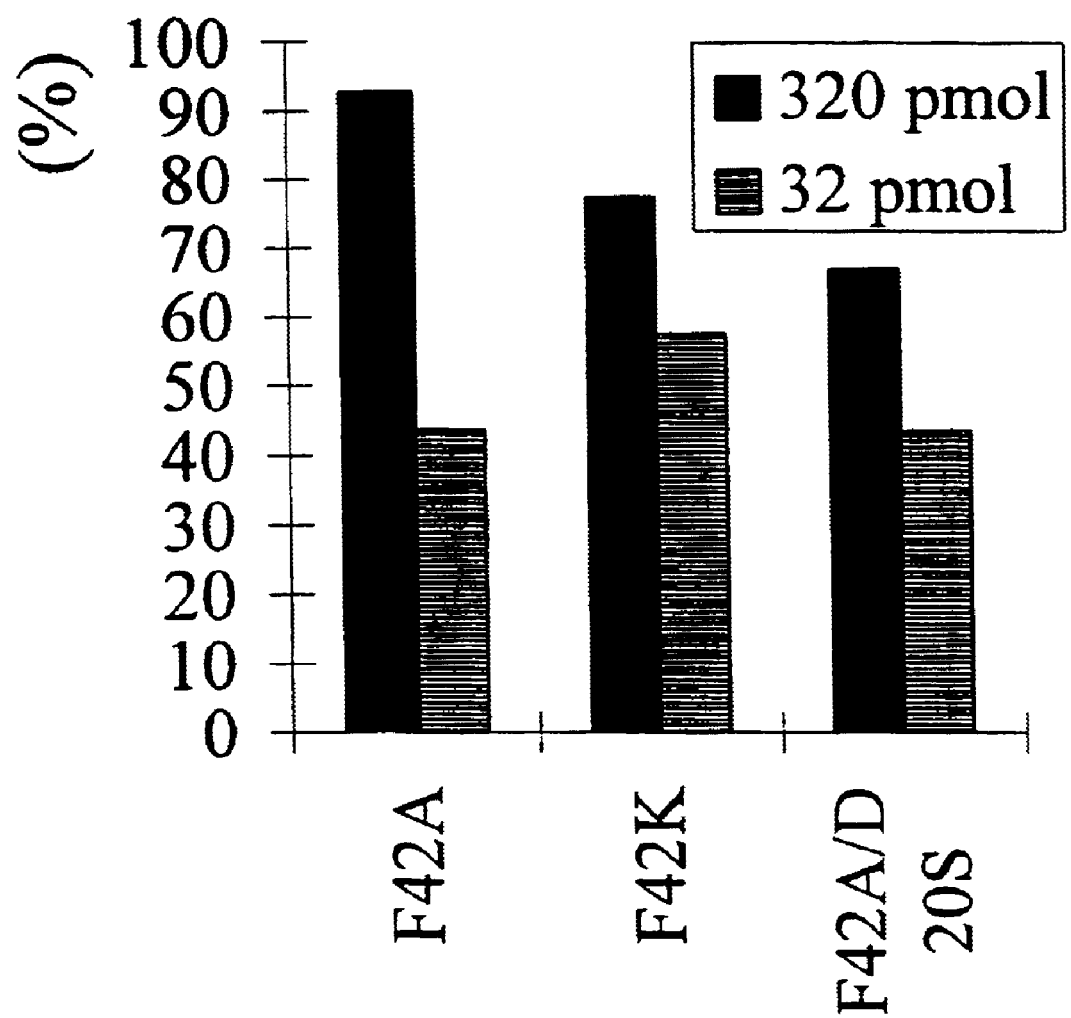

FIG. 15. Therapy of day 3 B16-C215 tumors in Vb3 TCR transgenic mice following treatment with 8 injections of C215FabSEA$_{D227A}$-Q-hIL2$_{F42A}$ (F42A), C215FabSEA$_{D227A}$-Q-hIL2$_{F42E}$ F42K or C215FabSEA$_{D227A}$-Q-hIL2$_{F42A/D20S}$ (F42A/D20S). Treatment was given daily for 8 consecutive days. On day 21 animals were sacrificed, and lung metastases counted. Ordinate: tumor reduction expressed in percentage.

Material and Methods

Recombinant DNA techniques and enzymes: Plasmid DNA preparations and other operations were performed essentially according to Sambrook et al. (Sambrook et al 1989). *E. coli* HB101 (Boyer et al 1969) was used as the host strain. Restriction endonucleases and the Klenow fragment of DNA polymerase I were obtained from Boehringer Mannheim or New England Biolabs, and used according to the suppliers recommendations. Taq-polymerase was obtained from Perkin Elmer. cDNA was made from the total RNA using the GeneAmp RNA PCR kit (Perkin-Elmer). Oligonucleotides were synthesized on a Gene Assembler (Pharmacia Biotech AB) or an ABI 392 DNA/RNA synthesizer (Applied Biosystems), and purified by reversed phase chromatography on the FPLC system (Pharmacia Biotech). Sequencing was done according to the dideoxy chain-termination principle (Sanger et al 1977) using Applied Biosystems Taq DyeDeoxy Termination Cycle Sequencing Kit and the products separated and detected on a DNA sequencer ABI 373A (Applied Biosystems). Bacteria harboring different plasmids were selected on plates containing 2×YT and 15 g agar base per liter, supplemented with 70 mg/L kanamycin, or 100 mg/L ampicillin. The liquid broth was 2×YT (per liter: 10 g yeast extract (Difco), 16 g tryptone (Difco) and 5 g NaCl).

TABLE I

| | | |
|---|---|---|
| LAKQ5 | ATA TAA GCT TCC ACC ATG GGC CAC ACA CGG AGG | (SEQ ID NO 1) |
| LAKQ7 | ACG CAG ATC TTT AGT TAT CAG GAA AAT GCT CTT GC | (SEQ ID NO 2) |
| LAKQ30 | TCA AAG CTT CTC GAG CGC GCT GTT ATC AGG AAA ATG CTC | (SEQ ID NO 3) |
| LAKQ37 | CGC GCG TCA GGC TAA CGA ACT GCC AGG CGC CCC GTC ACA GAG ACG A | (SEQ ID NO 4) |
| LAKQ38 | AGC TTC GTC TCA CGC GCG TTC TTC CTG TGA CGG GGC GCC TGG CAG TTC GTT AGC CTG ACG | (SEQ ID NO 5) |
| LAKQ88 | TGG TAC ACC ACA GAA GAC AGC TTG TAT GTA TG | (SEQ ID NO 6) |
| LAKQ89 | CAT ACA TAC AAG CTG TCT TCT GTG GTG TAC CA | (SEQ ID NO 7) |
| LAKQ90 | CGA ATA AGA AAG ACG TCA CTG TTC AGG AGT TGG | (SEQ ID NO 8) |
| LAKQ91 | CCA ACT CCT GAA CAG TGA CGT CTT TCT TAT TCG | (SEQ ID NO 9) |
| LAKQ92 | GAG ATA ATA AAG TTA TTA ACT CAG AAA ACA TG | (SEQ ID NO 10) |
| LAKQ93 | CAT GTT TTC TGA GTT AAT AAC TTT ATT ATC TC | (SEQ ID NO 11) |
| LAKQ108 | CGC GGA TCC GCG CGG CAC CAG GCC GCT GTT ATC CGG AAA ATG CTC TTG C | (SEQ ID NO 12) |
| LAKQ117 | CCG GAT AAC AGC GCG CGT CAG CTA ACG AAC TCC AGG CGC CCC GTC ACA GGA AGAA CGC CCG CAG GTC CAA CTG CA | (SEQ ID NO 13) |
| LAKQ118 | GTT GGA CCT GCG GGC GTT CTT CCT GTG ACG GGG CGC CTG GCA GTT CGT TAG CCT GAC GCG CGC TGT TAT | (SEQ ID NO 14) |

EXAMPLE 1

Biological Activity of CD80-C215Fab Fusion Proteins for Use in Costimulation of Tumor Therapy with Sag Targeted Fab Summary: CD80-C215Fab and CD80-C215Fab-SEAm57 fusion proteins have been constructed to contain the extracellular domain of human CD80. The fusion proteins were produced in mammalian cells, and tested for binding to CD28 using CHO cell transfectants and C215 antigen using Colo205 cells. Both fusion proteins bound to CD28 and C215 antigen, the later binding being 100-fold reduced compared to C215Fab-SEA. Since CD80 is linked to the N-terminal part of the L-chain it is possible that the CD80 moiety interferes with the C215Fab binding. Both fusion proteins costimulate SAG activated human T cells showing that the soluble CD80 retains its biological function.

Plasmid Constructions

The genes encoding a Fab fragment containing the variable domains of the murine antibody C215 were assembled as described previously (Dohlsten et al 1994). Cloning and mutagenesis of the staphylococcal enterotoxin A (SEA) gene yielding the replacements F47A and D227A has been described previously (Abrahmsén et al 1995). Three other mutations were introduced in the SEA gene using the primers LAKQ88-93 (all oligonucleotides used are compiled in Table I) to obtain SEA mutant 57. LAKQ5 and LAKQ7 were used in RT-PCR to introduce a Kozak box upstream, and to clone the gene encoding signal peptide and the extracellular part of human CD80 from human spleen total RNA. The nucleotide sequence was found to correspond to the gene bank sequence of CD80 (Accession number M27533). Two variants of the CD80 gene were made, having different cloning sites at the 3'-end: in separate PCRs the primers LAKQ30 and LAKQ108 were used to obtain a BssHII or a MroI site, respectively. A gene fusion encoding a CD80 fused before the kappa chain by a Q-linker (Wooton et al 1989), was constructed by inserting the DNA linker LAKQ37/38 BssHII-Esp3I, between the relevant CD80 gene and a DsaI site directly preceding the kappa gene. The plasmid pKGE987 was obtained by inserting the gene fusion encoding CD80-(Q-linker)-kappa, preceded by the CD80 signal peptide into a vector, which in addition to a CMV promoter and a poly A tail contains a neomycin gene to be used for selection of transformants. The last version of the CD80 gene was used to construct a gene fusion where it precedes the Fd-SEA mutant 57 gene fusion: a DNA fragment (LAKQ117/118) encoding a Q-linker was inserted between a MroI site in the CD80 gene and a PstI site at codon 4 and 5 in the C215 VH gene. This gene fusion was inserted in a second CMV promoter vector to yield the plasmid pMB189, thus encoding the CD80 signal peptide and extracellular portion followed by Fd and SEA mutant 57, connected by the three residue spacer GGP. In the plasmid pKGE961 the Fd gene has been inserted following a signal sequence (derived from another murine VH gene). The plasmid pMB156 encodes the native kappa chain, preceded by its native signal peptide, and contains the neomycin gene.

Production

Hamster embryonic kidney 293 cells were transfected with either pKGE961 and pKGE987, or with pMB156 and pMB189, to obtain cell lines producing CD80-C215Fab, and CD80-C215Fab-SEAm57, respectively. To obtain stable cell lines the selection medium was DMEM without phenol red (Pharmacia no MS 0127) supplemented with L-glutamine (GIBCO BRL no 25030-24), 10% bovine calf serum and Geneticin 1 mg/ml. The production medium was DMEM without phenol red supplemented with L-glutamin and 0.1% HSA (Pharmacia & Upjohn AB, Sweden). Fusion proteins were purified from the filtrated (Sartobran 0.65–0.4 um) culture media by affinity chromatography on protein G Sepharose FF (Pharmacia Biotech AB), followed by anti-CD80 affinity purification (immobilized anti-human CD80 antibody; Camfolio L307.4) or ion-exchange chromatography on SP Sepharose FF (Pharmacia Biotech).

Reagents. RPMII 1640 medium (Gibco, Middlesex, UK) supplemented with 2 mM L-glutamin (Gibco, Middlesex, UK), 0.01 M HEPES (Biological Industries, Israel), 1 mM NaHCO$_3$ (Biochrom KG, Berlin, Germany), 0.1 mg/ml gentamicin sulfate (Biological Industries, Kibbutz Beit Haemek, Israel), 1 mM sodium pyruvate (JRH Biosciences Industries, USA) and 10% heat inactivated fetal bovine serum (Gibco Middlesex, UK) was used as complete medium for all cell cultures.

Antibodies. mAbs directed to human CD57 (HNK1) and CD56 (HB55) were obtained from the mAb producing hybridoma cells (American Type Culture Collection, Rockville, Md.). Anti-mouse kappa chain mAb labelled with PE was obtained from Becton Dickinson (San Jose, Calif.).

Cells. Chinese hamster ovary (CHO) K1 cells were transfected with human cDNA encoding the CD28 gene at Pharmacia and Upjohn, Stockholm, Sweden. The transfectants were routinely analyzed for CD28 expression and maintained by FACS sorting at similar antigen expression levels. The human colon carcinoma cell line Colo205 was obtained from ATCC. All cell lines were free of mycoplasma.

T lymphocyte proliferation assay. T cells were obtained from human peripheral blood mononuclear cells (PBM) as previously described (Lando et al 1996) by negative selection panning with CD57, HLA-DR4, CD14 and CD56 mAbs. All tests on T cells were performed with $0.1 \times 10^6$ cells/well in 200 µl volumes, using flat-bottomed 96-well plates (Nunc, Roskilde, Denmark). DNA-synthesis was studies after exposure of cultures to [$^3$H]-thymidine [$^3$H] TdR (0.5 mCi/well) as described earlier (10).

Analysis by flow cytometry. Flow cytometric analysis and sorting were performed according to standard setting on a FACStar$^{Plus}$ flow cytometer (Becton Dickinson, Mountain View, Calif.). Due to the low affinity of CD80 to CD28 staining of CHO-CD28 cells with CD80-C215Fab fusion proteins were done omitting washes of the cells.

Cytokine assay. The production of IL-2 was analyzed using a IL-2 ELISA kit (huIL-2 Duoset, Genzyme).

Results.

Description of the CD80-Fab fusion proteins. The Fab moiety is of murine IgG1/k isotype although it contains the variable domains of the IgG2A/k monoclonal antibody C215 (Dohlsten et al 1995). The tripeptide sequence GGP follows the inter-chain disulphide forming cysteine in the CH1 domain. In the CD80-C215Fab-SEAm57 triple fusion protein, this functions as a spacer between Fd and a mutant of staphylococcal enterotoxin A (SEA; Betley et al 1988), having five substitutions. The replacements F47A and D227A were introduced to diminish affinity for MHC class II (Abrahamsén et al 1995), and the replacements N102Q, N149D and T218V were introduced to avoid fortuitous glycosylation when produced in eukaryotic cells. These latter replacements were selected with the aid of the X-ray structure (Sundström et al 1996). The final penta mutant was designated SEA mutant 57. Both fusion proteins contain the extracellular domain of human CD80 (defined to end FPDN). The native CD80 signal peptide was used and the mature protein found to start VIHV, as determined by amino acid sequencing of purified CD80-C215Fab. A spacer of 18 amino acids connects CD80 with the kappa chain in CD80-C215Fab, or the Fd portion of the Fab fragment in the CD80-C215Fab, or the Fd portion of the Fab fragment in the CD80-C215Fab-SEAm57 triple fusion protein. The spacers resemble a Q-linker (Wooton et al 1996) and have the sequences SARQANELPGAPSQEERA (SEQ ID NO 15) and SARQANELPGAPSQEERP (SEQ ID NO 16), respectively.

Facs analysis: Binding of CD80-C215Fab fusion proteins to CD28 positive cells and to C215 positive cells.

CD28 positive cells: CHO-CD28 cells were stained with CD80-C215Fab, CD80-C215Fab-SEAm57 or C215Fab-SEA followed by incubation with anti-mouse kappa chain mAb labeled with PE. The staining were done at 4° C. without any washes. Both the CD80-C215Fab and the triple fusion protein bound to CD28 expressed on the CHO cells in a dose dependent manner. No staining was, as expected, seen with the control fusion protein C215Fab-SEA.

C215 positive cells. The binding of the fusion proteins against the C215 antigen was evaluated against Colo205 cells. Colo205 cells were stained with CD80-C215Fab, CD80-C215Fab-SEAm57 or C215Fab-SEA followed by incubation with anti-mouse kappa chain mAb labeled with PE. The staining were done at 4° C. with three washes between each staining step.

Results (FIGS. 1–2): Both CD80-C215Fab and CD80-C215Fab-SEAm57 bound to the C215 antigen positive Colo205 cells in a dose dependent manner. The binding was 50–100 fold lower than that of C215Fab-SEA. This indicates that the introduction of CD80 in the N-terminal part of the fusion protein might interfere with the binding of the C215Fab part to the C215 antigen.

Dual fusions. Costimulation of superantigen activated T cells.

To determine the biological activity of the fusion proteins they were tested for costimulation of superantigen activated T cells.

Proliferation: T cells were incubated with Colo205 cells and 4 μM C242Fab-SEA and varying amounts of CD80-C215Fab for 4 days after which proliferation measured as incorporated $^3$H-thymidine was counted. The activity obtained without any CD80-C215Fab was 20039 cpm+/−1750.

IL-2 production: T cells were incubated with Colo205 cells and 4 μM C242Fab-SEA and varying amounts of CD80-C215Fab for 4 days after which the supernatant was harvested and the amount IL-2 was determined. The amount of IL-2 obtained without any CD80Fab-C215Fab was 2849 pg/ml.

Results (FIGS. 3–4): CD80-C215Fab costimulated the C242Fab-SEA induced activation of the T cells in a dose dependent manner both seen as proliferation and IL-2 production.

Triple Fusions. Costimulation of superantigen activated T cells.

To test the biological activity of the triple fusion protein, purified T cells were incubated with C215Fab-SEAm23 (m23 being the same SEA mutant affecting MHC class II binding that was used in the triple fusion protein, i.e. PHe47Ala/Asp227Ala) or CD80-C215Fab-SEAm57 presented on Colo205 cells. Proliferation: The incorporated $^3$H-thymidine was counted after 4 days. IL-2 production: The supernatants were harvested and the IL-2 content determined after 4 days.

Results (FIGS. 5–6): The triple fusion protein induced T cell activation and IL-2 production when presented on Colo205 cells. No such activity was seen with the C215Fab-SEAm23 indicating the importance of costimulation by CD80 for activation. Due to the lower binding affinity of the triple fusion protein (50–100× lower than that of C215Fab-SEA, see FACS data), the actual amount of C215Fab-SEAm23 bound to cells is likely to be substantially higher than that of the triple fusion protein.

EXAMPLE 2

Targeted IL-2 Potentiates and Prolongs the Effect of FabSEA on T Cell Activation and in Tumor Therapy Methods and Materials Construction of IL2 expression plasmids. The IL2 cDNA was cloned by RT-PCR using mRNA isolated from human peripheral blood mononuclear cells (PBM) which had been stimulated with the superantigen SEA for 24 hours. mRNA was isolated from $5\times10^6$ cells using a mRNA Direct kit from Dynal, Oslo according to the manufacturer's instructions. mRNA annealed to oligo(dT)$_{26}$-coated magnetic beads was eluted by heating to 95° C. Subsequently a PCR product was obtained by RT-PCR, taking advantage of the RT and DNA polymerase activities of Taq polymerase. ⅒ of the eluted mRNA was mixed with PCR primer IL2-1 and IL2-2 and a standard PCR reaction performed (30 rounds). The PCR product was subjected to agarose gel electrophoresis, the band excised from the gel and purified using the Prep-a-gene kit (Bio-Rad) kit. Following digestion with EcoRI and BamHI the fragment was cloned into EcoRI/BamHI-digested pBluescript KS II. The insert was sequenced and confirmed to be identical to the previously reported IL2 cDNA Taniguchi et al 1983). However, as a result of the PCR reaction a DNA segment encoding the Gly-Pro-Arg-Gln-Ala-Asn-Glu-Leu-Pro-Gly-Ala-Pro-Ser-Gln-Glu-Glu-Arg (SEQ ID NO: 23) "Gly-Pro-Q-linker" had been added 5' to the segment encoding mature human IL-2. Q-hIL2 was cloned into a plasmid from a house collection (cut with RsrII-KbaI) as a RsrII-NheI fragment. The resulting plasmid, pMS306, directs the secretion of C215FabSEA-Q-hIL2 to the periplasma of E. coli. The linkers between the moieties were further optimized as follows. A linker-encoding region, coding for Pro-Ala-Ser-Gly-Gly-Gly-Ala-Gly-Gly-Gly-Pro (SEQ ID NO:19) (replacing the original Gly-Gly-Pro) was introduced between the superantigen and the Fab moiety-encoding regions using site-directed mutagenesis. Similarly, the linkers Gly-Pro-Arg-Gln-Ser-Asn-Glu-Thr-Prol-Gly-Ser-Pro-Ser-Gln-Glu-Glu-Arg (SEQ ID NO: 20), Gly-Pro-Arg-Gln-Ala-Lys-Thr-Leu-Pro-Gly-Ala-Pro-Ser-Gln-Thr-Thr-Arg (SEQ ID NO: 21), or Gly-Pro-Thr-Glu-Ala-Asp-Glu-Leu-Pro-Gly-Ala-Pro-Ser-Glu-Glu-Glu-Thr (SEQ ID NO: 22) replaced the original Q-linker between the IL-2 and the Fab moiety. For combinations of dual fusion proteins, also constructs with IL-2 fused to the heavy or light chain, respectively, were compared.

Primers:

IL2-1:
5'-GCG GAT CCC GGT CCG CGT CAG GCT AAC GAA CTG CCA GGA GCT CCG TCT CAG GAA GAG CGT GCA CCT AC TTC AAG TTC TAC AAA G-3' (SEQ ID NO 17)

IL2-2:
5'-CCG AAT TCG CTA GCT TAT CAA GTT AGT GTT GAG ATG AT-3' (SEQ ID NO 18)

Expression of the fusion proteins in fermenter. Fusion proteins were expressed in the E. coli K-12 strain UL 635 (xyl-7, ara-14, T4$^R$, deltaompT) using a plasmid with a kanamycin resistance gene and lacUV5-promoter. Bacteria from frozen stock were incubated at 25° C. for approximately 21 h in shaker flasks containing (g/l) $(NH_4)_2SO_4$, 2.5; $KH_2PO_4$, 4.45; $K_2HPO_4$, 11.85; sodium citrate, 0.5; $MgSO_4\cdot7\ H_2O$, 1; glucose monohydrate, 11, 0.11 mM kanamycin and 1 ml/l trace element solution (Forsberg et al., 1989), however without $Na_2MoO_4\cdot2\ H_2O$. The cells were grown to an OD600 of 1–2 and 450 ml culture medium was used to inoculate a fermenter (Chemap, Switzerland) to a final volume of 5 l. The fermenter medium contained (g/l) $(NH_4)_2SO_4$, 2.5; $KH_2PO_4$, 9; $K_2HPO_4$, 6; sodium citrate, 0.5; glucose monohydrate, 22; $MgSO_4\cdot7\ H_2O$, 1; 0.11 mM kanamycin; 1 ml adecanol (Asahi Denka Kogyo K. K, Japan) and 1 ml/l trace element solution.

The pH was kept at 7.0 by titration with 25% ammonia, the temperature was 25° C. and aeration with atmospheric air 5 l/min. The partial pressure of dissolved $O_2$ was controlled to 30% by increasing agitation from 300 to 1000 rpm during batch phase and regulating the feed of 60% (w/v) glucose during fed batch phase. Product formation was induced at an OD$_{600}$ of 50 by adding 0.1 mM isopropyl β-D-thiogalactopyranoside, IPTG. After fermentation, the cells were removed by centrifugation at 800×g for 40 min at 4° C. The clarified medium was either analysed and purified directly or stored at −20° C.

Purification of fusion proteins. DNA present in the clarified medium was removed using precipitation with 0.19% polyethylenimine and 0.2 M NaCl during 30 min (Atkinson and Jack, 1973). After centrifugation as above, the supernatant was collected and the NaCl concentration adjusted to 0.5 M. This medium was applied to a Protein G Sepharose column (Pharmacia Biotech AB, Uppsala, Sweden) equilibrated with 10 mM sodium phosphate, 150 mM NaCl, pH 7.4 containing 0.05% Tween 80, PBST. The column was then washed with 5 column volumes PBST and bound protein was eluted with 0.1 M acetic acid, 0.02% Tween 80 pH 3.2. The pH of the sample was adjusted to 5.0 using 1 M Tris-HCl, pH 8.0, and applied to an SP Sepharose HP column (Pharmacia Biotech) equilibrated with 50 mM ammonium acetate, 0.02% Tween 80. The column was then washed with 2 column volumes equilibration buffer and the fusion protein eluted using a linear gradient from 50 to 500 mM ammonium acetate over 10 column volumes. For the C215Fab-IL2 fusion proteins, a pH of 6.0 was utilised while for the C215Fab-SEA-IL2 triple fusion proteins, the pH was 5.7 during the separation. The fusion proteins were filtered through a 0.22 μm filter and stored at −70° C. If more dilute, the eluate is concentrated to a final concentration of 0.5–1 mg/ml using Centricon 30 (Amicon) according to the manufacturer's instructions Cytotoxicity assays. MHC class II dependent and independent cytotoxicity assays were performed as previously described (Dohlsten et al., 1990). Briefly for MHC class II dependent assays $^{51}$Cr-labelled Raji cells (2500 cells per well in a final volume of 200 μl) were mixed with an SEA-dependent effector cell line generated by incubation of human PBM in the presence of low levels of recombinant hIL-2. Effector:Target cell ratio was 30:1. For MHC classII-independent assays $^{51}$Cr-labelled C215$^+$ colo205 cells (2500) were incubated with SEA-dependent effector cells at an E:T ratio of 45:1. $^{51}$Cr released into the medium was determined after 4 hours of incubation by scintillation counting.

In vitro co-stimulation assay on purified human T cells. Naive human T cells were purified essentially as described by Lando et al. (1993). Briefly, naive human T cells were purified from human blood PBM by Ficoll gradient centrifugation, followed by separation over gelatine columns, and lastly negative selection by panning in petri dishes containing HNK1 and HLA-DR mAbs. Proliferation experiments using naive human T cells was performed essentially as described by Lando et al. (1996). Briefly, naive T cells (100.000 cells per well) were combined with irradiated CHO transfectants (10.000 cells per well) in a total volume of 200 μl RPMI-1640 with supplements (Lando et al 1993). For experiments with IL-2 containing fusion proteins, cells were incubated for 7 days in the presence of 1 nM of the indicated substances. On the final day of the experiment the cells were pulsed with $^3$H-Thymidine to measure incorporation into DNA of dividing cells.

Therapy of B16-C215 tumors. Therapy was performed essentially as described previously (Dohlsten et al 1994; Hansson et al 1997). On day 0 C57Bl/6 mice were injected i.v. into the tail vein with 75000–150000 syngeneic B16-F10 melanoma cells. These B16 cells were expressing the human GA-733 antigen recognized by the C215 mAb. On day 1, 3 or 5 therapy with C215Fab proteins were initiated. On day 21 the experiment was terminated, at which time the lungs were removed and disseminated lung tumors counted.

Immunohistochemistry was performed on lungs of animals carrying Day 18 B16-C215 tumors essentially as described previously (Dohlsten et al 1995). Samples were taken out 4 hours after the final injection. Stained area was determined manually.

Immunopharmacology was performed essentially as described (Rosendahl et al 1996). Spleens from C57 Bl/6 mice having received 1 or 3 injections, once daily, were removed 48 hours after the final injection and SEA-dependent cytotoxicity determined, using Raji cells as targets in a standard $^{51}$Cr release assay as described above. E:T ratio was 100:1.

Results and Discussion

Production and purification of IL2-containing fusion proteins. An E. coli expression vector encoding a C215FabSEA-Q-hIL2 triple fusion protein was constructed. This vector encodes the two subunits of the triple fusion protein on a bi-cistronic mRNA transcribed from the LacUV5 promotor. Each of the two subunits are preceded by a signal peptide directing export to the periplasmic space of E. coli. The first subunit is VH of the C215Fab followed by a Gly-Gly-Pro linker (VH-C$_H$1-Gly-Gly-Pro-SEA). The other subunit is VK of C215Fab followed by CK of the C242Fab, which is linked to human IL2 by a Gly-Pro-Q-linker (Vk-Ck-Gly-Pro-Q-hIL2). The Gly-Pro-Q-linker sequence (SEQ ID NO: 23) is a slightly modified version of a natural linker found in the OmpR E. coli protein (Wootton et al 1989). See materials and method for more complete information. Also a C215Fab-Q-hIL2 fusion protein was produced. It is identical to C215FabSEA-Q-hIL2 except that the Gly-Gly-Pro-SEA moiety of the protein has been removed. The corresponding DNA sequence in the expression vector is deleted accordingly. Mutated derivatives of C215FabSEA-Q-hIL2 were generated by PCR-mediated site-directed mutagenesis by standard methods to produce a number of proteins such as C215FabSEA$_{D227A}$-Q-hIL2 and C215FabSEA$_{D227A}$-Q-hIL2$_{F42A}$. In later variants of the triple fusion protein the intersubunit cystine is replaced by two serine residues. This alterations does not affect the biological activity.

Plasmids encoding IL2-containing proteins were transformed into the E. coli production strain UL635, and fermentation subsequently performed. Fusion proteins were purified from the culture medium using protein G affinity chromatography. Degraded variants of the fusion proteins were removed using ion exchange chromatography. The products obtained were at least 90% full-length fusion protein, as determined by SDS-PAGE (material and methods). Using the optimal design of the fusion protein, up to 130 mg/l fusion protein is obtained in the growth medium and typically 70 mg triple fusion protein was obtained from 1 liter medium.

Functional characterization of IL2-containing Fab fusion proteins. The ability of IL2-containing fusion proteins such as C215FabSEA-Q-hIL2 and C215Fab-Q-hIL2 fusion proteins to induce proliferation of the IL-2 dependent murine cell line CTLL-2 was essentially similar to that of recombinant human IL2 on a molar basis (data not shown). Moreover, antigen-binding and SEA activity of C215FabSEA-Q-hIL2 and C215FabSEA were found to be indistinguishable in a number of assays, suggesting that there were no adverse effects of introducing IL2 into the molecule. These assays included ability to induce MHC classII-independent killing of the C215$^+$ human colon cancer cell line colo205 by an SEA-reactive T cell effector cell line in a 4 hour $^{51}$Cr-release assay. Also MHC class II-dependent killing of MHC classII$^+$ Raji (rat lymphoma) cells by SEA-reactive effector T cells proceed with similar efficiencies (data not shown). More direct evidence for uncompromised C215 antigen and MHC class II binding was obtained by FACS analysis. The dose dependence of C215FabSEA and C215FabSEA-Q-hIL2 binding to Raji cells was found to be similar on a molar basis (data not shown). Also dose-dependent binding of C215FabSEA-Q- hIL2 and C215Fab-Q-hIL2 to colo205 cells was found to be similar to that observed for C215FabSEA (data not shown), indicating that antigen-binding was uncompromised in the IL2-containing fusion proteins.

IL2-dependent proliferation induced by FabSEA. Resting human T cells require both a signal 1 and a signal 2 to trigger optimal T cell proliferation and activation (Schwartz, 1990). Superantigens can deliver signal 1, if presented on a cell. IL-2 being the major downstream effector of B7/CD28 signalling is expected to give signal 2.

Here we show using resting T cells purified from human blood that a C215FabSEA-Q-hIL2 triple fusion protein or C215FabSEA in combination with C215Fab-Q-hIL2 or recombinant human IL-2 does indeed induce T cell proliferation in vitro (FIG. 7)

Resting human T cells were incubated with targeted SEA (C215FabSEA or C215FabSEA-Q-hIL2) in the presence of IL2 (in the form of C215Fab-Q-hIL2, C215FabSEA-Q-hIL2 or recombinant human IL-2). SEA was presented on irradiated CHO cells transfected with C215 antigen (via the Fab part), MHC classII/Dr which binds SEA. Untransfected CHO cells served as control. After 7 days of incubating T cells with CHO transfectants and the substances in question proliferation was measured by incorporation of $^3$H-Thymidine into DNA.

C215FabSEA-Q-hIL2 induced the proliferation of human T cells when presented on CHO cells transfected with the human C215 antigen (CHO-C215), which the Fab is directed against (FIG. 7). Likewise, proliferation was induced when the protein was presented on CHO-Dr (human MHC class II), whereas no proliferation was observed in the presence of untransfected CHO cells (CHO) or in the absence of CHO cells (R10). C215FabSEA or C215Fab-Q-hIL2 did not induce any significant proliferation by themselves when presented on CHO cells, indicating that both SEA and IL-2 are indeed necessary for induction of proliferation. This was confirmed, as the combination of C215FabSEA and C215Fab-Q-hIL2 or C215FabSEA and recombinant human IL2 induced a qualitatively similar effect to the one induced by C215FabSEA-Q-hIL2. This also shows that in this assay IL-2 is necessary but, unlike SEA, it does not need not be cell bound.

C215FabSEA-Q-hIL2 as well as the combination of C215FabSEA and C215Fab-Q-hIL2 causes enhanced and sustained T cell activation and improved tumor infiltration in vivo. Both C215Fab-Q-hIL2+C215FabSEA, and C215FabSEA-Q-hIL2 were much more potent inducers of T cell activation than C215FabSEA as measured by the ability to induce SEA-dependent killing of target cells (FIG. 8). Briefly, mice received 1 or 3 injections administered daily of the indicated proteins. Two days after the last injection spleens from treated mice were taken out and cytotoxic activity against SEA-coated Raji cells determined in a standard 4 hr $^{51}$Cr release assay.

Both C215FabSEA-Q-hIL2 and C215FabSEA/C215Fab-Q-hIL2 induced not only enhanced but also sustained T cell activation. Levels of serum cytokines such as IFNgamma., which dips drastically after the fourth injection of C215FabSEA stays at a very high level even after the fourth injection of C215FabSEA-Q-hIL2 (data not shown). In general, IFNgamma and TNFalpha levels were much higher (up to 10×) higher than in the case of C215FabSEA.

Figure 9:
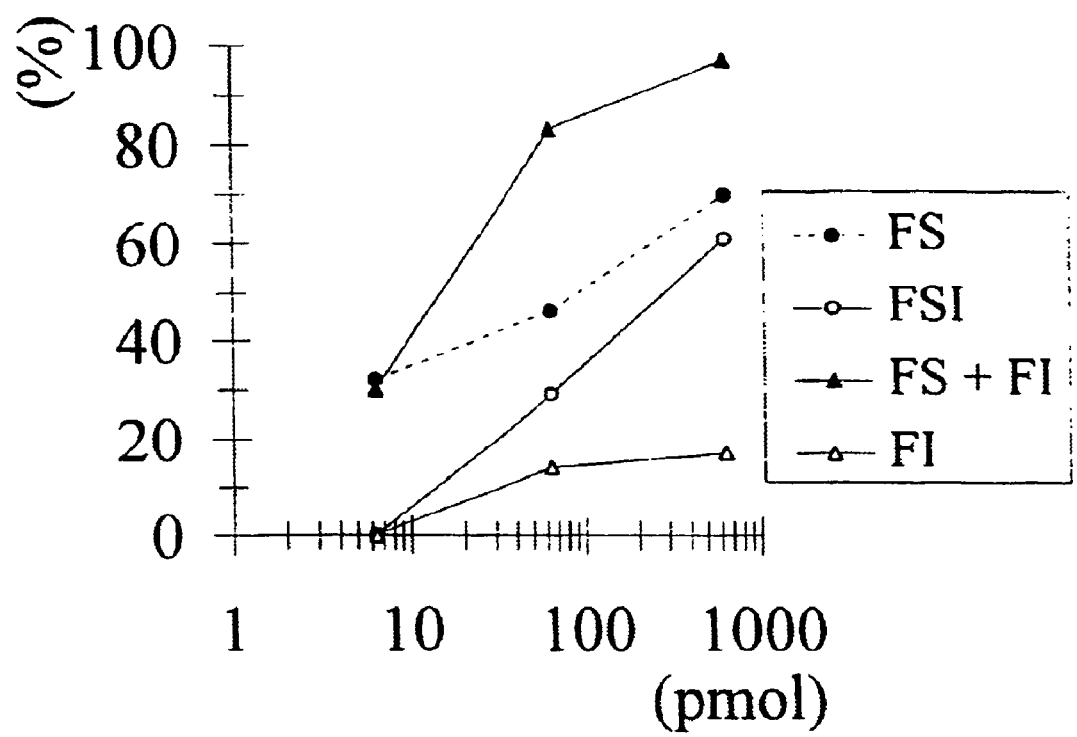

Improved therapy of established B16-C215 tumors with C215FabSEA and C215Fab-Q-hIL2 combination treatment. The effects of IL2-potentiation of FabSag tumor therapy was investigated in the murine B16 melanoma model (FIG. 9). In the shown example 8–12 week old C57 Bl/6 female mice were inoculated on day 0 with 150.000 B16 cells transfected with the human tumor antigen GA-733, which the C215 mAb is directed against (B16-C215 in the following). The indicated substances were injected on days 5, 6 and 7. Each datapoint corresponds to 7 animals. On day 21 the animals were sacrificed, and the number of melanin-pigmented B16 tumors colonizing the lung counted. Combination of C215FabSEA and C215Fab-Q-hIL2 in several experiments were shown to induce better therapy than C215FabSEA as compared to a non-treated control (FIG. 9). In the indicated experiment, C215FabSEA/C215Fab-Q-hIL2 combination treatment gave better therapeutic effect than the C215FabSEA-Q-hIL2 triple fusion protein.

Subsequent immunohistochemistry studies revealed that C215FabSEA alone or combination of C215FabSEA and C215Fab-Q-hIL2 gave rise to similar numbers of B16-C215 tumor-infiltrating CD4 and CD8 T cells. Interestingly, however, the number of CD25 (IL2Ra) positive cells—a good marker for T cell activation—dramatically increased between the $3^{rd}$ and $4^{th}$ injection of C215FabSEA/C215Fab-Q-hIL2 (FIG. 10). In contrast, it decreased in the case of C215FabSEA indicating beginning anergy. The quality of infiltrating T cells thus seems to be higher in the case of combination treatment than C215FabSEA alone, which may help to explain the improved therapeutic effect. Likewise, serum cytokines such as Interferon γ produced secondary to T cell activation decrease markedly after the fourth injection of FabSEA (FIG. 11). With a FabSEA-Q-hIL2 triple fusion protein, however, the Interferon levels stay at a high level even after the fourth injection. This observation provides an additional indication that including IL-2 in the construct can counteract Fab-SEA induced T cell anergy.

Improved therapy of B16-C215 tumors with C215FabSEA$_{D227A}$-Q-hIL2. Superantigens are much more toxic in humans than in mice, in part because the affinity for MHC class II in humans is considerably higher (Hansson et al 1997). Systemic toxicity of FabSEA proteins is thus expected to be the major limitation for therapy in humans. One way to increase local activation in the tumor (Fab-dependent) versus systemic immune-activation (SEA-MHC classII dependent) would be to decrease the affinity of SEA for MHC classII. Based on the crystal structure of SEA we made a mutant of C215FabSEA, C215FabSEA$_{D227A}$, with 100-fold reduced affinity for MHC class II. Unlike wt C215Fab-SEA it does not have the capacity to cross-link MHC classII molecules, which is believed to be a major reason for SEA-mediated systemic toxicity (Hansson et al 1997).

The window between efficient therapy and toxicity in treatment of day 1 B16-C215 tumors in Vb3 TCR transgenic mice was at least 50-fold wider for the C215FabSEA$_{D227A}$ mutant as compared to C215FabSEA (Hansson et al 1997). In accordance with this observation, immunohistochemistry revealed that at doses of the two proteins resulting in similar therapy, comparable immune activation in the tumor was observed, whereas much less systemic immune activation was observed in the spleen with C215FabSEA$_{D227A}$ (Hansson et al 1997). Moreover, pharmacokinetic studies in rabbits showed a dramatic reduction in the targeting of C215FabSEA$_{D227A}$ to the spleen and other lymphoid organs, where most of the MHC classII$^+$ cells are located, as compared to C215FabSEA (data not shown).

For clinical use a Fab-SEA-IL2 triple fusion protein is expected to contain a mutated superantigen. We therefore made a C215FabSEA$_{D227A}$-Q-hIL2 triple fusion protein. The produced protein was able to induce the proliferation of resting human T cells (data not shown)—and induced sustained SEA-dependent CTL activity in mice for up to 6 injections (FIG. 12). In contrast, background CTL activity was observed with C215FabSEA$_{D227A}$ (<10%—data not shown) and C215Fab-Q-hIL2 (<15%—data not shown). Therapy of established (day 3) B16-G733 tumors in normal C57 Bl/6 mice with 8 injections of this protein administered daily gave as good therapy as an optimal dose of C215FabSEA (FIG. 13). In this system C215FabSEA$_{D227A}$, which is designed for optimal activity in humans not mice, does only have minor effects (FIG. 13). At the highest dose, some toxicity of C215FabSEA$_{D227A}$-Q-hIL2 was encountered, however. In contrast, several therapy experiments indicate that combination of C215FabSEA$_{D227A}$ and C215Fab-Q-hIL2 (8 injections) does also lead to substantially improved therapy of day 3 B16-GA733 tumors in Vb3 TCR transgenic mice when compared to C215FabSEA$_{D227A}$ alone (data not shown). In Vb3 TCR transgenic mice >90% of T cells react with SEA, as opposed to 10–20% in normal mice. Interestingly, in rabbits repeated injections (up to 8) of C215FabSEA$_{D227A}$-Q-hIL2 (0/4 rabbits dead after repaeated injections at 20 μg/kg) does not appear to be more toxic than C215FabSEA$_{D227A}$ without IL-2 (0/4 rabbits dead after repaeated injections at 20 μg/kg; 4/4 ; dead at 20 μg/kg) and much less toxic than C215FabSEA (1/4 rabbits dead after repaeated injections at 1 μg/kg). At the same time, sustained immune activation (lymphocyte rebound effect) is observed only after treatment with C215FabSEA$_{D227A}$-Q-hIL2 but not with C215FabSEA$_{D227A}$ or C215FabSEA—indicating that indeed inclusion of IL-2 helps to counteract FabSEA-induced T cell anergy (data not shown).

Therapy of B16-C215 tumors with IL-2 mutated C215FabSEA$_{D227A}$-Q-hIL2 proteins. The greater toxicity, and in the case of C215FabSEA-Q-hIL2 lower therapeutic efficacy, of IL2-containing triple fusion proteins may in part be due to "retargeting" of the SEA activity to lymphoid tissues. This retargeting effect is ascribed to the high affinity of IL2 (Kd=10 pM) for its receptor, which is mainly found on T cells in the spleen and other lymphoid tissues. To address this question we have made derivatives of C215FabSEA$_{D227A}$-Q-hIL2 in which the IL-2 moiety is mutated in order to reduce the affinity for $IL2R^+$ cells and thus systemic activation. In principle the same approach that was used to improve the therapeutic window for the C215FabSEA$_{D227A}$ protein.

Interaction between IL-2 and its high-affinity receptor is very well studied. The receptor consists of three subunits a, b and g. Cross-linking of b and g is required for biological activity, whereas the a subunit is required for optimal binding. Our strategy is to reduce affinity of IL-2 for its high-affinity receptor (abg) by eliminating a-subunit binding, and subsequently reduce, but not eliminate, b and g-subunit binding as necessary.

Three such mutants of C215FabSEA$_{D227A}$-Q-hIL2 were designed to eliminate IL2Ra-binding (F42A, F42K) and in addition impair IL2Rb binding (F42A/D20S). These proteins have 100-(F42A), 1000-(F42K) and 3000-fold (F42A/D20S) reduced activity, respectively, in inducing proliferation of the IL-2 dependent murine cell-line CTLL-2. Experiments are in progress to determine in more detail the properties of these proteins, in particular with respect to affinity and on-rates for binding to activated human T cells and the IL2 receptor. Initial therapy experiments indicate that such a strategy is promising (FIG. 14; FIG. 15). In the shown examples, 8 injections were given to Vb3 TCR transgenic mice (where >90% of T cells are activated by SEA) carrying day 3 B16-GA733 tumors. Although some toxicity was still observed at the highest dose, it came later when C215FabSEA$_{D227A}$-Q-hIL2$_{F42A}$ or C215FabSEA$_{D227A}$-Q-hIL2 was used ($6^{th}$ injection) and treatment at the highest dose consistently leads to more than 90% tumor reduction when compared to a PBS-treated control (FIG. 14). We are currently exploring this highly promising approach by introducing additional mutations into the SEA and IL2 parts to further improve the therapy to toxicity window.

Moreover, work is in progress to make C215FabSEA-Q-hIL2 triple fusion proteins comprising a Thr51Pro mutation in the IL-2 part (Chang et al 1996). This mutation may serve to block IL2R-mediated internalization of the fusion protein without reducing IL-2 bioactivity. This is likely to be important because it will reduce the removal of fusion protein by this pathway, and thus increase local concentration and efficacy of the drug. Thr51Pro mutated proteins may contain further mutations in the SEA and IL-2 parts to reduce affinity for MHC classII and the IL2 receptor, respectively.

EXAMPLE 3

Experiments for Verifying Effects of (Sag, IM)-Conjugates. Target Cells IM-Receptor Positive or MHC Class II Positive Cells A Sag-IM molecule may bind to cells expressing MHC class II, thus facilitating SDCC. Alternatively, cells expressing the receptor for IM may be targeted. It is therefore possible that a Sag-IM molecule could be useful for inducing the killing of undesired cells expressing the receptor for IM.

A C215FabSEA-hIL2 triple fusion protein can be considered a Sag-IM molecule in the event that neither effector nor target cell express the antigen recognized by the C215Fab. Effector cells would be T cells of the right Vβ subtype. Target cells could e.g. be abberrant hemapoietic cells expressing the IL2 receptor such as those present in certain leukemias or lymphomas.

Exp. A: In vitro proof-of-concept: Effector T cells (human T cells repeatedly stimulated with SEA) and target cells (f.ex. human "Raji" B cell lymphoma cells) will be incubated with C215FabSEA-IL2 triple fusion protein mutated to reduce binding to MHC class I. This is the standard set up for SDCC assays (effector T cells, Raji cells, experimental substance). We have actually found that a C215FabSEA$_{D227A}$ in killing of Raji cells. An obvious explanation for the increased potency is that the triple fusion protein is presented on IL2 receptors expressed on Raji cells.

Exp. B: In vivo proof-of-concept: Murine lymphoma models (such as the RBL-5 lymphoma in C57 Bl/6 mice) are well established (Hoglund et al J Exp Med 168, 1469–1474). Targeting of the IL-2 receptor or another IM-R with a Sag-IM protein in such models could provide proof-of-concept for targeting IM-receptor positive cells in vivo.

Sag-IM targeting of IM-R positive cells is complicated by the fact that both effector and target cells frequently express the receptor for IM. Nevertheless, under certain circumstances this mode of therapy may be efficacious. Factors such as density of IM-R expression on target cells, number and location of target cells, etc. is likely to play a role. It should also be emphasized that e.g. the IL2R alpha is only up-regulated upon T cell activation—there might thus be a temporal window during which IM-R is expressed at high abundancy on target cells, but not on the effector cells.

Sag-IM fusion proteins in which Sag stands for a wild-type superantigen mutated to a reduced affinity for MHC Class II may similarly be used.

REFERENCES

*labelled articles may be found more related to immune modulators than the others Abrahmsén L et al (1995) Characterization of two distinct MHC Class II binding sites in the superantigen staphylococcal enterotoxin A. EMBO J 14:2978–86.

Abrahmsén et al (1996) WO 9601650 (patent application). A conjugate between a modified superantigen and a target-seeking compound and the use of the conjugate.

Antonsson P et al (1996) Staphylococcal enterotoxin A and E chimera with reduced seroreactivity and retained ability to target cytotoxic T cells for use in tumor therapy. ABRF '96: Biomolecular Techniques, Holiday Inn Golden Gateway, San Francisco, Calif. Mar. 30–Apr. 2, 1996.

Antonsson et al (1996) J. Immunol. 158:4245–4251.

Antonsson et al (1997) WO 9736932 (patent application)

Atkinson et al (1973) Biochim. Biophys. Acta 308:41–52.

*Bamborough et al. (1994) Structure 2:839–51.

*Becker et al (1996) Eradication of human hepatic and pulmonary melanoma metastases in SCID mice by antibody-interleukin 2 fusion proteins. Proc. Natl. Acad. Sci. USA 93:2702–2707.

*Belfrage Thesis (1996) Activation of murine cytotoxic cells with interleukin-2 and the bacterial superantigen staphylococcal enterotoxin A. University of Lund, Sweden (Augusti/September 1996).

*Belfrage et al (1994) Combined activation of murine lymphocytes with staphylococcal enterotoxin and interleukin-2 results in additative cytotoxic activity. Cancer Immunol. Immunother 38:265–271).

*Belfrage et al (1995) Enhanced and prolonged efficacy of superantigen-induced cytotoxic T-lymphocyte activity by IL-2 in vivo. Cancer Immuno. Immunother. 41:87–94.

*Belfrage et al (1997a) Prevention of superantigen induced downregulation of T cell mediated cytotoxic activity by IL-2 in vivo. Immunology 90:183–188.

*Belfrage et al (1997b) Prevention of superantigen induced tolerance in vivo by IL-2 treatment. Cancer Immunol. Immunother. 44:77–82.

*Berndt et al (1994) Biochemistry 33:6571–7.

Betley et al (1988) Nucleotide sequence of the type A staphylococcal enterotoxin gene. J. Bacteriol. 170:34–41.

Boyer et al (1969) A complementation analysis of the restriction and modification of DNA in *Escherichia coli*. J. Mol. Biol. 41:459–472.

Blanco et al (1990) Mutants of staphylococcal toxic shock syndrome toxin 1: Mitogenicity and recognition by a neutralizing monoclonal antibody. Infect. Immun. 58 (1990) 3020–3028.

Carlsson et al (1985) Kinetics of IL-2 and interferon-gamma production, expression of IL-2 receptors, and cell proliferation in human mononuclear cells exposed to staphylococcal enterotoxin A. Cell. Immunol. 96:175–183.

*Chen et al (1992) Costimulation of antitumor immunity by the B7 counter receptor for the T lymphocyte molecules CD28 and CTLA. Cell 71:1093–102.

*Chang et al (1996) A point mutation in Interleukin-2 that alters ligand internalization. J. Biol. Chem. 271:13349–13355.

*Collins et al (1988) Proc. Natl. Acad. Sci. USA 85:7709–13.

Dohlsten et al (1988) Two subsets of human peripheral blood $CD4^+$ T helper cells differing in the capacity to produce IL-2 and interferon-gamma can be defined by the Leu-18 and monoclonal antibodies. Eur. J. Immunol. 18:1173–1178.

Dohlsten et al (1990) Immunology 71:96–100.

Dohlsten M et al (1991) Monoclonal antibody-targeted superantigens: A different class of anti-tumor agents. Proc. Natl. Acad. Sci. USA 88:9287–9291.

Dohlsten et al (1992) WO 9201470 (patent application). Target specific antibody-superantigen conjugates and their preparation.

Dohlsten M et al (1994) Monoclonal antibody-superantigen fusion proteins: Tumor specific agents for T cell based tumor therapy. Proc. Natl. Sci. USA 91:8945–8949.

Dohlsten et al (1995) Proc. Natl. Acad. Sci. U.S.A. 92:9791–9795.

*Dow et al (1996) WO 9636366 (patent application) Combined gene therapy with the gene for a superantigen and the gene for a cytokine or chemokine.

*Fell et al EP 439095 (patent application).

Fleury S et al (1991) Mutational analysis of the interaction between CD4 and class II MHC: class II antigens. Cell 66:1037–49.

Forsberg G et al (1989) BioFactors, 2, 105–112.

Hansson J et al (1997) Proc. Natl. Acad. Sci.-U.S.A.:2489–94.

Kalland et al (1991) WO 9104053 (patent application). Pharmaceutical composition that makes cells expressing MHC Class II antigens targets for cytotoxic cells.

Kappler J W et al (1992) Mutations defining functional regions of the superantigen staphylococcal enterotoxin B. J. Exp. Med. 175:387–396

Kappler et al (1993) WO 9314634 (patent application). Protective effects of mutated superantigens.

Kotzin B L et al (1993) Superantigens and their potential role in human disease. Adv. Immunol. 54:99–166.

Lamphear J G et al (1996) Residues near the amino and carboxy termini of staphylococcal enterotoxin E independently mediate TCRVβ specific interactions. J. Immunol. 156: 2178–2185 (Mar. 15, 1996)

*Lando P A et al (1993) Co-stimulation with B7 and targeted superantigen is required for MHC class II-independent T-cell proliferation but not cytotoxicity. Immunology 80: 236–241.

*Lando et al (1996) Regulation of superantigen-induced T cell activation in the absence and the presence of MHC class II. J. Immunol. 157:2857–2863.

Lindholm et al (1993) 9301302 (patent application). Tumor, carbohydrate antigen specific monoclonal antibody and cell line.

Newel et al (1991) In vivo T-cell activation by staphylococcal enterotoxin B prevents outgrowth of a malignant tumor. proc. Natl. Acad. Sci. USA 88:1074–1078.

Ochi et al (1993) J. Immunol. 151:3180–3186

*Pancook et al (1996) Eradication of established hepatic human neuroblastoma metastases in mice with severe combines immunodeficiency by antibody targeted interleukin-2. Cancer Immunol. Immunother. 42:88–92.

*Pouletty (1993) EP 510949 (patent application) Targeted cytolysis.

*Rosenblum et al EP 396387 (patent application).

*Rosendahl et al (1996) Int. J. Cancer 68, 109–113.

Sanger et al (1977) DNA sequencing with chain-terminating inhibitors. Proc. Natl. Acad. Sci. USA 74: 5463–5467, 1977.

Sambrook et al (1989) Molecular Cloning, A laboratory manual, 2nd ed. Cold Spring Harbor Laboratory Press.

*Schwartz (1990) Science 248:1349–1356.

Stern et al (1989) WO 8907947 (patent application). Improvements relating to antigens.

Sundström et al (1996) J. Biol. Chem. 271:32212–32216.

*Taniguchi et al (1983) Structure and expression of a cloned cDNA for human Interleukin-2. Nature 302:305–310.

*Terman et al (1991) WO 9110680 (patent application). Tumor killing effects of enterotoxins and related compounds.

*Terman et al (1993) WO 9324136 (patent application). Tumor killing effects of enterotoxins and related compounds.

Woodworth (1993) Preclinical and Clinical development of Cytokine toxins presented at the conference "Molecular approaches to cancer Immunotherapy", Ashville, N.C., Nov. 7–11, 1993.

Wootton et al (1989) Prot. Eng. 2:535–543.

Zurawski et al (1993) EMBO J. 12:5113–9.

SEQUENCE LISTING

<160> NUMBER OF SEQ ID NOS: 23

<210> SEQ ID NO 1
<211> LENGTH: 33
<212> TYPE: DNA
<213> ORGANISM: ARTIFICIAL SEQUENCE
<220> FEATURE:
<221> NAME/KEY: misc_feature
<222> LOCATION: (1)..(33)
<223> OTHER INFORMATION: DNA primer for use in RT-PCR.

<400> SEQUENCE: 1
atataagctt ccaccatggg ccacacacgg agg                33

<210> SEQ ID NO 2
<211> LENGTH: 35
<212> TYPE: DNA
<213> ORGANISM: ARTIFICIAL SEQUENCE
<220> FEATURE:
<221> NAME/KEY: misc_feature
<222> LOCATION: (1)..(35)
<223> OTHER INFORMATION: DNA primer for use in RT-PCR.

<400> SEQUENCE: 2
acgcagatct ttagttatca ggaaaatgct cttgc              35

<210> SEQ ID NO 3
<211> LENGTH: 39
<212> TYPE: DNA
<213> ORGANISM: ARTIFICIAL SEQUENCE
<220> FEATURE:
<221> NAME/KEY: misc_feature
<222> LOCATION: (1)..(39)
<223> OTHER INFORMATION: DNA primer for use in RT-PCR.

<400> SEQUENCE: 3
tcaaagcttc tcgagcgcgc tgttatcagg aaaatgctc          39

<210> SEQ ID NO 4
<211> LENGTH: 46
<212> TYPE: DNA
<213> ORGANISM: ARTIFICIAL SEQUENCE
<220> FEATURE:
<221> NAME/KEY: misc_feature
<222> LOCATION: (1)..(46)
<223> OTHER INFORMATION: DNA primer for use in RT-PCR.

<400> SEQUENCE: 4
cgcgcgtcag gctaacgaac tgccaggcgc cccgtcacag agacga   46

<210> SEQ ID NO 5
<211> LENGTH: 60
<212> TYPE: DNA
<213> ORGANISM: ARTIFICIAL SEQUENCE
<220> FEATURE:
<221> NAME/KEY: misc_feature
<222> LOCATION: (1)..(60)
<223> OTHER INFORMATION: DNA primer for use in RT-PCR.

<400> SEQUENCE: 5
agcttcgtct cacgcgcgtt cttcctgtga cggggcgcct ggcagttcgt tagcctgacg        60

<210> SEQ ID NO 6
<211> LENGTH: 32
<212> TYPE: DNA
<213> ORGANISM: ARTIFICIAL SEQUENCE
<220> FEATURE:
<221> NAME/KEY: misc_feature
<222> LOCATION: (1)..(32)
<223> OTHER INFORMATION: DNA primer for use in RT-PCR.

<400> SEQUENCE: 6
tggtacacca cagaagacag cttgtatgta tg                                      32

<210> SEQ ID NO 7
<211> LENGTH: 32
<212> TYPE: DNA
<213> ORGANISM: ARTIFICIAL SEQUENCE
<220> FEATURE:
<221> NAME/KEY: misc_feature
<222> LOCATION: (1)..(32)
<223> OTHER INFORMATION: DNA primer for use in RT-PCR.

<400> SEQUENCE: 7
catacataca agctgtcttc tgtggtgtac ca                                      32

<210> SEQ ID NO 8
<211> LENGTH: 33
<212> TYPE: DNA
<213> ORGANISM: ARTIFICIAL SEQUENCE
<220> FEATURE:
<221> NAME/KEY: misc_feature
<222> LOCATION: (1)..(33)
<223> OTHER INFORMATION: DNA primer for use in RT-PCR.

<400> SEQUENCE: 8
cgaataagaa agacgtcact gttcaggagt tgg                                     33

<210> SEQ ID NO 9
<211> LENGTH: 33
<212> TYPE: DNA
<213> ORGANISM: ARTIFICIAL SEQUENCE
<220> FEATURE:
<221> NAME/KEY: misc_feature
<222> LOCATION: (1)..(33)
<223> OTHER INFORMATION: DNA primer for use in RT-PCR.

<400> SEQUENCE: 9
ccaactcctg aacagtgacg tctttcttat tcg                                     33

<210> SEQ ID NO 10
<211> LENGTH: 32
<212> TYPE: DNA
<213> ORGANISM: ARTIFICIAL SEQUENCE
<220> FEATURE:
<221> NAME/KEY: misc_feature
<222> LOCATION: (1)..(32)
<223> OTHER INFORMATION: DNA primer for use in RT-PCR.

<400> SEQUENCE: 10
gagataataa agttattaac tcagaaaaca tg                                      32

<210> SEQ ID NO 11
<211> LENGTH: 32
<212> TYPE: DNA
<213> ORGANISM: ARTIFICIAL SEQUENCE

```
<220> FEATURE:
<221> NAME/KEY: misc_feature
<222> LOCATION: (1)..(32)
<223> OTHER INFORMATION: DNA primer for use in RT-PCR.

<400> SEQUENCE: 11
catgttttct gagttaataa ctttattatc tc                                    32

<210> SEQ ID NO 12
<211> LENGTH: 49
<212> TYPE: DNA
<213> ORGANISM: ARTIFICIAL SEQUENCE
<220> FEATURE:
<221> NAME/KEY: misc_feature
<222> LOCATION: (1)..(49)
<223> OTHER INFORMATION: DNA primer for use in RT-PCR.

<400> SEQUENCE: 12
cgcggatccg cgcggcacca ggccgctgtt atccggaaaa tgctcttgc                  49

<210> SEQ ID NO 13
<211> LENGTH: 77
<212> TYPE: DNA
<213> ORGANISM: ARTIFICIAL SEQUENCE
<220> FEATURE:
<221> NAME/KEY: misc_feature
<222> LOCATION: (1)..(77)
<223> OTHER INFORMATION: DNA Primer for use in RT-PCR.

<400> SEQUENCE: 13
ccggataaca gcgcgcgtca ggctaacgaa ctcccaggcg ccccgtcaca ggaagaacgc      60
ccgcaggtcc aactgca                                                    77

<210> SEQ ID NO 14
<211> LENGTH: 69
<212> TYPE: DNA
<213> ORGANISM: ARTIFICIAL SEQUENCE
<220> FEATURE:
<221> NAME/KEY: misc_feature
<222> LOCATION: (1)..(69)
<223> OTHER INFORMATION: DNA primer for use in RT-PCR.

<400> SEQUENCE: 14
gttggacctg cgggcgttct tcctgtgacg gggcgcctgg cagttcgtta gcctgacgcg      60
cgctgttat                                                             69

<210> SEQ ID NO 15
<211> LENGTH: 18
<212> TYPE: PRT
<213> ORGANISM: ARTIFICIAL SEQUENCE
<220> FEATURE:
<221> NAME/KEY: misc_feature
<222> LOCATION: (1)..(18)
<223> OTHER INFORMATION: Designated peptide to act as a spacer between
      the kappa chain or the Fd portion of the Fab fragment in a fusion
      protein.  The spacer resembles a Q-linker

<400> SEQUENCE: 15

Ser Ala Arg Gln Ala Asn Glu Leu Pro Gly Ala Pro Ser Gln Glu Glu
1               5                   10                  15

Arg Pro

<210> SEQ ID NO 16
<211> LENGTH: 18
<212> TYPE: PRT
<213> ORGANISM: ARTIFICIAL SEQUENCE
```

```
<220> FEATURE:
<221> NAME/KEY: misc_feature
<222> LOCATION: (1)..(18)
<223> OTHER INFORMATION: Designated peptide to act as a spacer between
      the kappa chain or the Fd portion of the Fab fragment in a fusion
      protein.  The spacer resembles a Q-linker

<400> SEQUENCE: 16

Ser Ala Arg Gln Ala Asn Glu Leu Pro Gly Ala Pro Ser Gln Glu Glu
1               5                   10                  15

Arg Pro

<210> SEQ ID NO 17
<211> LENGTH: 84
<212> TYPE: DNA
<213> ORGANISM: ARTIFICIAL SEQUENCE
<220> FEATURE:
<221> NAME/KEY: misc_feature
<222> LOCATION: (1)..(84)
<223> OTHER INFORMATION: DNA Primer for use in RT-PCR

<400> SEQUENCE: 17
gcggatcccg gtccgcgtca ggctaacgaa ctgccaggag ctccgtctca ggaagagcgt      60
gcacctactt caagttctac aaag                                             84

<210> SEQ ID NO 18
<211> LENGTH: 38
<212> TYPE: DNA
<213> ORGANISM: ARTIFICIAL SEQUENCE
<220> FEATURE:
<221> NAME/KEY: misc_feature
<222> LOCATION: (1)..(38)
<223> OTHER INFORMATION: DNA Primer for use in RT-PCR.

<400> SEQUENCE: 18
ccgaattcgc tagcttatca agttagtgtt gagatgat                              38

<210> SEQ ID NO 19
<211> LENGTH: 11
<212> TYPE: PRT
<213> ORGANISM: ARTIFICIAL SEQUENCE
<220> FEATURE:
<221> NAME/KEY: misc_feature
<222> LOCATION: (1)..(11)
<223> OTHER INFORMATION: Designated peptide to act as a Q-linker.

<400> SEQUENCE: 19

Pro Ala Ser Gly Gly Gly Gly Ala Gly Gly Pro
1               5                   10

<210> SEQ ID NO 20
<211> LENGTH: 17
<212> TYPE: PRT
<213> ORGANISM: ARTIFICIAL SEQUENCE
<220> FEATURE:
<221> NAME/KEY: misc_feature
<222> LOCATION: (1)..(17)
<223> OTHER INFORMATION: Designated peptide to act as a Q-linker.

<400> SEQUENCE: 20

Gly Pro Arg Gln Ser Asn Glu Thr Pro Gly Ser Pro Ser Gln Glu Glu
1               5                   10                  15

Arg

<210> SEQ ID NO 21
<211> LENGTH: 17
```

```
<212> TYPE: PRT
<213> ORGANISM: ARTIFICIAL SEQUENCE
<220> FEATURE:
<221> NAME/KEY: misc_feature
<222> LOCATION: (1)..(17)
<223> OTHER INFORMATION: Designated peptide to act as a Q-linker.

<400> SEQUENCE: 21

Gly Pro Arg Gln Ala Lys Thr Leu Pro Gly Ala Pro Ser Gln Thr Thr
1               5                   10                  15

Arg

<210> SEQ ID NO 22
<211> LENGTH: 17
<212> TYPE: PRT
<213> ORGANISM: ARTIFICIAL SEQUENCE
<220> FEATURE:
<221> NAME/KEY: misc_feature
<222> LOCATION: (1)..(17)
<223> OTHER INFORMATION: Designated peptide to act as a Q-linker.

<400> SEQUENCE: 22

Gly Pro Thr Gly Ala Asp Glu Leu Pro Gly Ala Pro Ser Glu Glu Glu
1               5                   10                  15

Thr

<210> SEQ ID NO 23
<211> LENGTH: 17
<212> TYPE: PRT
<213> ORGANISM: ARTIFICIAL SEQUENCE
<220> FEATURE:
<221> NAME/KEY: misc_feature
<222> LOCATION: (1)..(17)
<223> OTHER INFORMATION: Designated peptide to act as a Q-linker.

<400> SEQUENCE: 23

Gly Pro Arg Gln Ala Asn Glu Leu Pro Gly Ala Pro Ser Gln Glu Glu
1               5                   10                  15

Arg
```

What is claimed is:

1. A method for inactivating a target cell in the presence of T cells comprising bringing the target cell and a T cell in contact with a superantigen in the presence of an immune modulator wherein at least one of the superantigen and immune modulator is conjugated to a targeting moiety that targets the target cell.

2. The method of claim 1, wherein the superantigen and immune modulator are both conjugated to the same targeting moiety, the conjugate being a triple conjugate.

3. The method of claim 1, wherein the superantigen and targeting moiety are conjugated.

4. The method of claim 3, wherein the immune modulator is not conjugated to the targeting moiety.

5. The method of claim 1, wherein the target cell is inactivated in vivo in an individual having a disease associated with the target cell.

6. The method of claim 5, wherein the disease is cancer.

7. The method of claim 1, wherein the targeting moiety is selected from the group consisting of an antibody, an antigen-binding fragment of an antibody, an Fab fragment of an antibody, an Fab₂ fragment of an antibody, or a single chain antibody.

8. The method of claim 1, wherein the superantigen is modified to have a decreased ability to bind to MHC class II antigen compared to the corresponding wild type superantigen.

9. The method of claim 1, wherein the superantigen is modified to have decreased seroreactivity in human sera compared to the corresponding wild type superantigen.

10. The method of claim 1, wherein the superantigen is chimeric comprising sequences derived from two or more wild type superantigens.

11. The method of claim 1, wherein the immune modulator is selected from the group consisting of cytokines, chemokines, and extracellular parts of lymphocyte bound receptors and ligands.

12. The method of claim 1, where in the immune modulator is IL-2.

* * * * *